United States Patent
Legendy et al.

(10) Patent No.: US 12,389,950 B2
(45) Date of Patent: Aug. 19, 2025

(54) FIXED DOSE CARTRIDGE FOR VAPORIZER DEVICE

(71) Applicant: Pax Labs, Inc., San Francisco, CA (US)

(72) Inventors: Conrad Legendy, San Francisco, CA (US); Maya Voskoboynikov, San Francisco, CA (US); Colt Stander, Millbrae, CA (US); Pradyumna Upadhya, San Jose, CA (US); Katherine Murphy, San Francisco, CA (US)

(73) Assignee: PaxLabs, Inc.

( * ) Notice: Subject to any disclaimer, the term of this patent is extended or adjusted under 35 U.S.C. 154(b) by 286 days.

(21) Appl. No.: 16/837,850

(22) Filed: Apr. 1, 2020

(65) Prior Publication Data

US 2020/0315253 A1    Oct. 8, 2020

Related U.S. Application Data

(60) Provisional application No. 62/828,333, filed on Apr. 2, 2019.

(51) Int. Cl.
*A24F 40/57* (2020.01)
*A24F 40/10* (2020.01)
(Continued)

(52) U.S. Cl.
CPC .............. *A24F 40/57* (2020.01); *A24F 40/10* (2020.01); *A24F 40/20* (2020.01); *A24F 40/42* (2020.01);
(Continued)

(58) Field of Classification Search
CPC .......... A24F 40/10; A24F 40/20; A24F 40/42; A24F 40/53; A24F 40/57; A24F 40/60; A24F 40/65; A61M 11/042; A61M 15/008; A61M 15/0081; A61M 15/06; A61M 2205/3561; A61M 2205/50; A61M 2205/52
See application file for complete search history.

(56) References Cited

U.S. PATENT DOCUMENTS 11,206,869 B2    12/2021    Selby et al.
11,606,970 B2    3/2023    Fu et al.
(Continued)

FOREIGN PATENT DOCUMENTS

WO    WO-20190173923 A1    9/2019

OTHER PUBLICATIONS

International Search Report and Written Opinion, mailed Jul. 8, 2020, International Patent Application PCT/US2020/026251 filed Apr. 1, 2020, 17 pages.

*Primary Examiner* — Joseph D. Boecker
(74) *Attorney, Agent, or Firm* — FisherBroyles, LLP

(57) ABSTRACT

Features relating to vaporizer devices configured to provide a fixed amount of aerosol for user consumption are provided. In particular, aspects of the current subject matter relate to utilizing data associated with a cartridge to identify an amount of aerosol to be generated by a vaporizer device, and applying to a heating element an amount of energy to achieve the desired amount of aerosol. Dose control settings may be enabled to provide for the vaporizer device to generate a number of doses based on a selected dose size.

20 Claims, 10 Drawing Sheets

(51) Int. Cl.
*A24F 40/20* (2020.01)
*A24F 40/42* (2020.01)
*A24F 40/53* (2020.01)
*A24F 40/60* (2020.01)
*A24F 40/65* (2020.01)
*A61M 11/04* (2006.01)
*A61M 15/00* (2006.01)
*A61M 15/06* (2006.01)

(52) U.S. Cl.
CPC .............. *A24F 40/53* (2020.01); *A24F 40/65* (2020.01); *A61M 11/042* (2014.02); *A61M 15/008* (2014.02); *A24F 40/60* (2020.01); *A61M 15/0081* (2014.02); *A61M 15/06* (2013.01); *A61M 2205/3561* (2013.01); *A61M 2205/50* (2013.01); *A61M 2205/52* (2013.01)

(56) References Cited

U.S. PATENT DOCUMENTS

| | | | |
|---|---|---|---|
| 11,698,717 B2 | 7/2023 | Amorde et al. | |
| 11,744,965 B2 | 9/2023 | Alarcon | |
| 12,004,568 B2 | 6/2024 | O'Hare et al. | |
| 12,263,299 B2 | 4/2025 | Cohen | |
| 2012/0048266 A1* | 3/2012 | Alelov | A61M 15/0065 128/203.14 |
| 2013/0319435 A1* | 12/2013 | Flick | A61M 11/041 219/490 |
| 2014/0190496 A1* | 7/2014 | Wensley | A24F 40/485 131/273 |
| 2014/0270727 A1* | 9/2014 | Ampolini | A24F 40/50 392/394 |
| 2015/0208731 A1 | 7/2015 | Malamud et al. | |
| 2016/0143361 A1* | 5/2016 | Juster | H05B 1/0244 392/404 |
| 2016/0157524 A1* | 6/2016 | Bowen | G01N 33/0027 702/50 |
| 2017/0014582 A1 | 1/2017 | Skoda | |
| 2017/0042251 A1* | 2/2017 | Yamada | A61M 11/042 |
| 2018/0043114 A1* | 2/2018 | Bowen | A61M 15/003 |
| 2018/0177231 A1* | 6/2018 | Woodbine | H04L 67/12 |
| 2018/0263288 A1* | 9/2018 | Goldstein | A61M 11/042 |
| 2019/0158938 A1 | 5/2019 | Bowen et al. | |
| 2019/0217027 A1* | 7/2019 | Freeman | A61M 15/0085 |
| 2020/0000143 A1 | 1/2020 | Anderson et al. | |
| 2020/0022416 A1* | 1/2020 | Alarcon | A61M 15/0028 |
| 2020/0146361 A1 | 5/2020 | Silver et al. | |
| 2020/0352249 A1 | 11/2020 | Achtien et al. | |
| 2021/0011446 A1 | 1/2021 | Anderson et al. | |
| 2021/0015158 A1* | 1/2021 | Moloney | A61M 15/002 |
| 2021/0346617 A1* | 11/2021 | Wagner | A61M 15/0083 |
| 2022/0071294 A1 | 3/2022 | Cabigon et al. | |

* cited by examiner

410

| Total Energy Consumed 401 | Fixed Dose Cartridge Identifier 402 | Dose Size 403 | Target Maximum Energy 404 | Cartridge Lock Identifier 405 | Number of Doses Consumed 406 |
|---|---|---|---|---|---|
| 0 | 1 | 1,000 | 300,000 | 0 | 0 |

| Total Energy Consumed 401 | Fixed Dose Cartridge Identifier 402 | Dose Size 403 | Target Maximum Energy 404 | Cartridge Lock Identifier 405 | Number of Doses Consumed 406 |
|---|---|---|---|---|---|
| 1,000 | 1 | 1,000 | 300,000 | 0 | 1 |

| Total Energy Consumed 401 | Fixed Dose Cartridge Identifier 402 | Dose Size 403 | Target Maximum Energy 404 | Cartridge Lock Identifier 405 | Number of Doses Consumed 406 |
|---|---|---|---|---|---|
| 5,000 | 1 | 4,000 | 300,000 | 0 | 5 |

| Total Energy Consumed 401 | Fixed Dose Cartridge Identifier 402 | Dose Size 403 | Target Maximum Energy 404 | Cartridge Lock Identifier 405 | Number of Doses Consumed 406 |
|---|---|---|---|---|---|
| 9,000 | 1 | 4,000 | 300,000 | 0 | 6 |

| Total Energy Consumed 401 | Fixed Dose Cartridge Identifier 402 | Dose Size 403 | Target Maximum Energy 404 | Cartridge Lock Identifier 405 | Number of Doses Consumed 406 |
|---|---|---|---|---|---|
| 301,000 | 1 | 4,000 | 300,000 | 1 | 80 |

FIG. 4E

| Total Energy Consumed 601 | Number of Doses Consumed 602 | Dose Size Setting 603 | Dose Size 604 | Target Maximum Energy 605 | Target Maximum Number of Doses 606 | Dose Control 607 | Last Dose Time/Date 608 |
|---|---|---|---|---|---|---|---|
| 0 | 0 | | | | | | - |
| 1,000 | 1 | 1 | 1,000 | 500,000 | 500 | 1 | Mar 4 2020 21:42:05.012 |
| 5,000 | 5 | 1 | 1,000 | 500,000 | 500 | 1 | Mar 4 2020 21:44:20.672 |
| 9,000 | 9 | 4 | 4,000 | 500,000 | 500 | 1 | Mar 4 2020 21:47:14.208 |
| 502,000 | 502 | 4 | 4,000 | 500,000 | 500 | 1 | Apr 20 2020 19:23:15.420 |

FIG. 6

FIXED DOSE CARTRIDGE FOR VAPORIZER DEVICE

CROSS-REFERENCE TO RELATED APPLICATIONS

This application claims priority to U.S. Provisional Patent Application No. 62/828,333, filed Apr. 2, 2019 and entitled "Fixed Session Cartridge for Vaporizer Device," the content of which is incorporated in its entirety by reference herein.

TECHNICAL FIELD

The current subject matter described herein relates generally to vaporizer devices, such as portable, personal vaporizer devices for generating and delivering an inhalable aerosol from one or more vaporizable materials, and more particularly relates to vaporizer devices configured to deliver a fixed or preselected amount of aerosol.

BACKGROUND

Vaporizing devices, including electronic vaporizers or e-vaporizer devices, allow the delivery of vapor and aerosol containing one or more active ingredients by inhalation of the vapor and aerosol. Electronic vaporizer devices are gaining increasing popularity both for prescriptive medical use, in delivering medicaments, and for consumption of nicotine, tobacco, other liquid-based substances, and other plant-based smokeable materials, such as cannabis, including solid (e.g., loose-leaf or flower) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Aspects of the current subject matter relate to delivering to a user a fixed or preset amount of aerosol from a vaporizer device. Additional aspects of the current subject matter relate to generating and providing aerosol consumption and related information to the user.

According to an aspect of the current subject matter, a method includes obtaining, by a controller of a vaporizer device, data indicative of a preset amount of aerosol to generate for a use of the vaporizer device, the vaporizer device having a cartridge, and the data indicative of the preset amount of aerosol associated with the cartridge and accessible to the controller; and applying, by the controller and to a heating element in the cartridge, an amount of energy correlated with the preset amount of aerosol to generate the preset amount of aerosol. The cartridge contains therein a vaporizable material from which aerosol is generated by heating of the vaporizable material.

According to an inter-related aspect, a vaporizer device includes at least one data processor and at least one memory storing instructions which, when executed by the at least one data processor, cause operations including obtaining data indicative of a preset amount of aerosol to generate for a use of the vaporizer device, the vaporizer device having a cartridge, and the data indicative of the preset amount of aerosol associated with the cartridge and accessible to the at least one data processor; and applying, to a heating element in the cartridge, an amount of energy correlated with the preset amount of aerosol to generate the preset amount of aerosol. The cartridge contains therein a vaporizable material from which aerosol is generated by heating of the vaporizable material.

According to an inter-related aspect, a non-transitory computer readable medium is provided, the non-transitory computer readable medium storing instructions, which when executed by at least one data processor, result in operations including obtaining, by a controller of a vaporizer device, data indicative of a preset amount of aerosol to generate for a use of the vaporizer device, the vaporizer device having a cartridge, and the data indicative of the preset amount of aerosol associated with the cartridge and accessible to the controller; and applying, by the controller and to a heating element in the cartridge, an amount of energy correlated with the preset amount of aerosol to generate the preset amount of aerosol. The cartridge contains therein a vaporizable material from which aerosol is generated by heating of the vaporizable material.

In some variations, one or more of the features disclosed herein including the following features can optionally be included in any feasible combination. The data indicative of the preset amount of aerosol may include a value of the amount of energy to be applied to generate the preset amount of aerosol. The data indicative of the preset amount of aerosol may be stored on a near-field communication tag contained on at least a portion of the cartridge, where the controller is configured to access data stored on the near-field communication tag. One or more of a value of total energy consumed, a fixed dose cartridge identifier, a value of dose size, a value of target maximum energy, a cartridge lock identifier, a number of doses consumed, a dose size setting, a target number of doses, a dose control setting, and a time and date stamp may be associated with the cartridge and accessible to the controller. The application of the amount of energy may be based on one or more of the fixed dose cartridge identifier, the cartridge lock identifier, and the dose control setting. Following the application of the amount of energy, one or more of the value of total energy consumed, the number of doses consumed, and the time and date stamp may be modified. Based on the value of total energy consumed and the value of target maximum energy, a number of doses remaining in the cartridge may be determined. In response to a determination of no doses remaining in the cartridge, the cartridge lock identifier may be modified. One or more of the data indicative of the preset amount of aerosol, the value of total energy consumed, the fixed dose cartridge identifier, the value of dose size, the value of target maximum energy, the cartridge lock identifier, the number of doses consumed, the dose size setting, the target number of doses, the dose control setting, and the time and date stamp may be provided to a user device for display on the user device. The preset amount of aerosol may be one or more of a preconfigured amount and adjustable by a user through an application executed on a user device in communication with the controller.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4A-FIG. 4E illustrate example representations of data for a fixed dose cartridge consistent with implementations of the current subject matter;

FIG. 6 illustrates example representations of data for a fixed dose cartridge consistent with implementations of the current subject matter;

When practical, similar reference numbers denote similar structures, features, or elements.

DETAILED DESCRIPTION

Figure 1A:
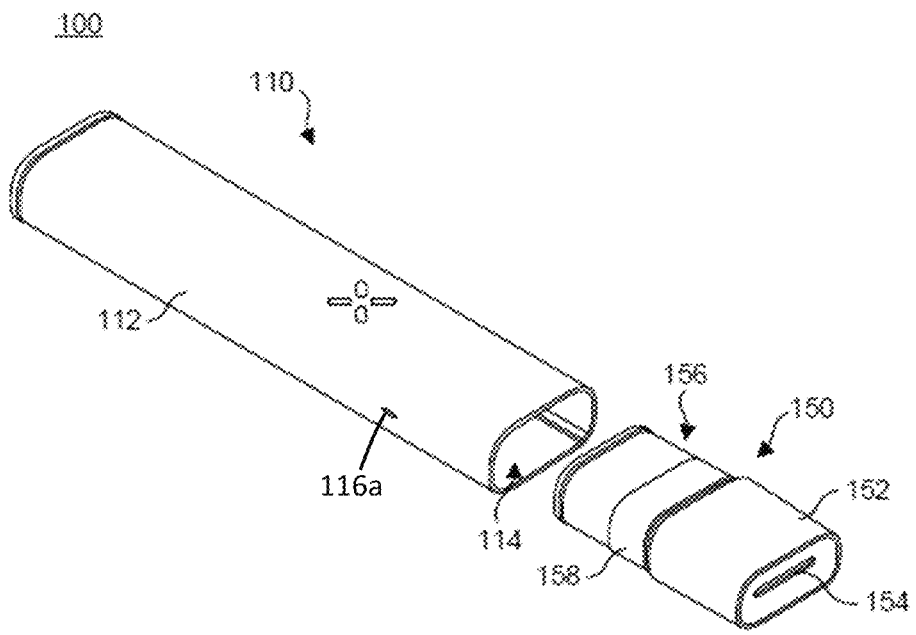
FIG. 1A-FIG. 1F illustrate features of a vaporizer device including a vaporizer body and a cartridge consistent with implementations of the current subject matter.

Aspects of the current subject matter relate to delivering to a user a fixed amount of aerosol from a vaporizer device. Additional aspects of the current subject matter relate to generating and providing aerosol consumption and related information to the user.

The amount of aerosol generated by vaporization of a vaporizable material contained in a cartridge of a vaporizer device for consumption by a user may vary between uses and cartridges. For example, factors such as amount of energy applied, temperature settings, characteristics or properties of the vaporizable material (such as viscosity, age or date of production, chemical composition, concentrations, etc.), and/or usage data (such as date of production of the cartridge, frequency of use of the cartridge, date and time of last use of the cartridge 150, number of doses completed, etc.) may contribute to and affect the amount of aerosol generated for user consumption.

Aspects of the current subject matter provide for delivering a fixed amount of aerosol to a user by controlling operation of the vaporizer device and by monitoring and updating data associated with use of the vaporizer device. By monitoring the data associated with use of the vaporizer device, and in particular the cartridge, and linking or associating that data to the cartridge, the amount of vaporizable material remaining in the cartridge may be tracked. Moreover, by receiving a selection or indication of the fixed amount of aerosol to generate, the vaporizer device consistent with implementations of the current subject matter may generate the fixed amount and update the data associated with the cartridge to reflect the usage. In particular, data mapped to or associated with the cartridge of the vaporizer device is utilized to provide the fixed amount of aerosol to the user. A controller of the vaporizer device uses the mapped or associated data to appropriately control generation of the aerosol, as further described herein.

Implementations of the current subject matter refer to doses of aerosol for consumption. According to aspects of the current subject matter, a dose is defined as a fixed amount of aerosol generated by the vaporizer device for consumption by the user as a number of puffs taken by the user until the fixed amount of aerosol is consumed or inhaled. In some implementations, a dose may also be referred to as a session; and the terms dose and session may be used interchangeably herein. In some instances, a dose is fixed or selected by an entity, such as a manufacturer or distributor of the cartridge or the vaporizer device, or a care giver, medical facility, and/or the like for controlling consumption by the user. In some instances, the dose is user adjustable and/or user configurable. In some instances, the dose is represented by a dose size and/or a dose size setting. The dose may be correlated with amount of energy supplied to a heating element of the cartridge, as further described herein.

Before providing additional details regarding aspects of a vaporizer device delivering a fixed amount of aerosol, the following provides a description of some examples of vaporizer devices including a vaporizer body and a cartridge in which aspects of the current subject matter may be implemented. The following descriptions are meant to be exemplary, and aspects related to the prediction of vapor production by a vaporizer device consistent with the current subject matter are not limited to the example vaporizer devices described herein.

Implementations of the current subject matter include devices relating to vaporizing of one or more materials for inhalation by a user. The term "vaporizer" may be used generically in the following description and may refer to a vaporizer device, such as an electronic vaporizer. Vaporizers consistent with the current subject matter may be referred to by various terms such as inhalable aerosol devices, aerosolizers, vaporization devices, electronic vaping devices, electronic vaporizers, vape pens, etc. Examples of vaporizers consistent with implementations of the current subject matter include electronic vaporizers, electronic cigarettes, e-cigarettes, or the like. In general, such vaporizers are often portable, hand-held devices that heat a vaporizable material to provide an inhalable dose of the material. The vaporizer may include a heater configured to heat a vaporizable material which results in the production of one or more gas-phase components of the vaporizable material. A vaporizable material may include liquid and/or oil-type plant materials, or a semi-solid like a wax, or plant material such as leaves or flowers, either raw or processed. The gas-phase components of the vaporizable material may condense after being vaporized such that an aerosol is formed in a flowing air stream that is deliverable for inhalation by a user. The vaporizers may, in some implementations of the current subject matter, be particularly adapted for use with an oil-based vaporizable material, such as cannabis-derived oils although other types of vaporizable materials may be used as well.

One or more features of the current subject matter, including one or more of a cartridge (also referred to as a vaporizer cartridge or pod) and a reusable vaporizer device body (also referred to as a vaporizer device base, a body, a vaporizer body, or a base), may be employed with a suitable vaporizable material (where suitable refers in this context to being usable with a device whose properties, settings, etc. are configured or configurable to be compatible for use with the vaporizable material). The vaporizable material may include one or more liquids, such as oils, extracts, aqueous or other solutions, etc., of one or more substances that may be desirably provided in the form of an inhalable aerosol. The cartridge may be inserted into the vaporizer body, and then the vaporizable material heated which results in the inhalable aerosol.

Figure 1B:
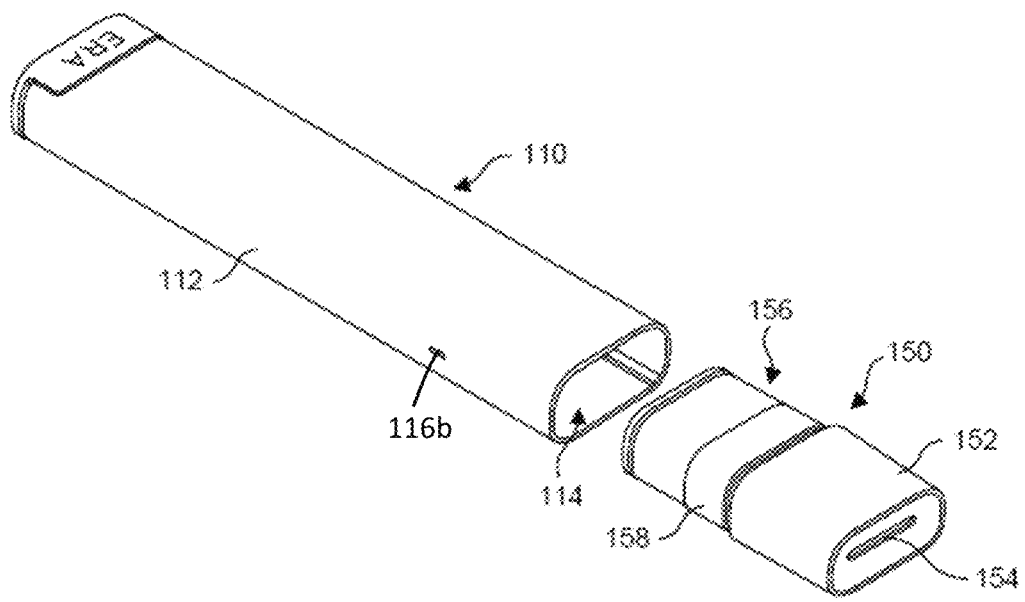
Figure 1C:
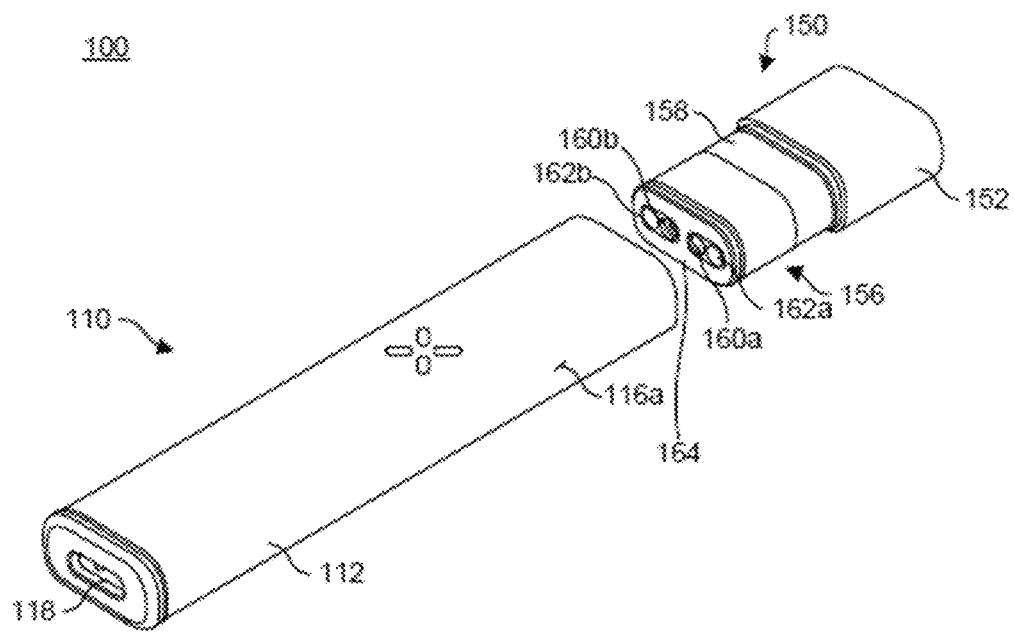
Figure 1D:
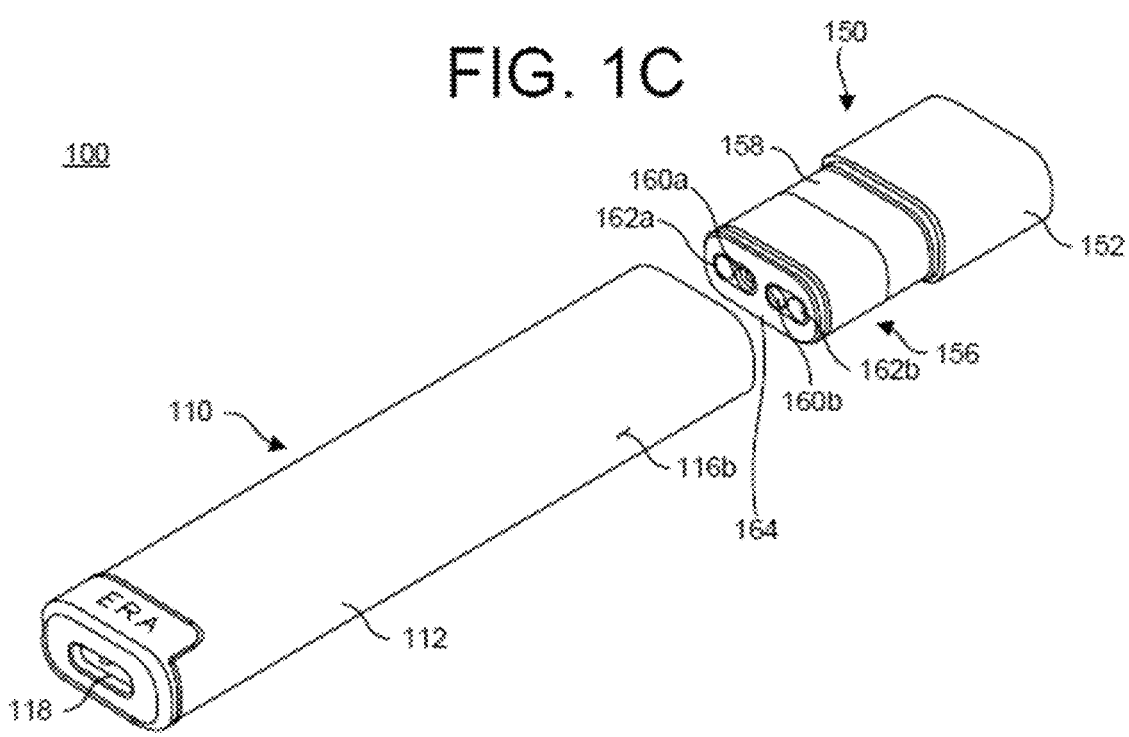
Figure 1E:
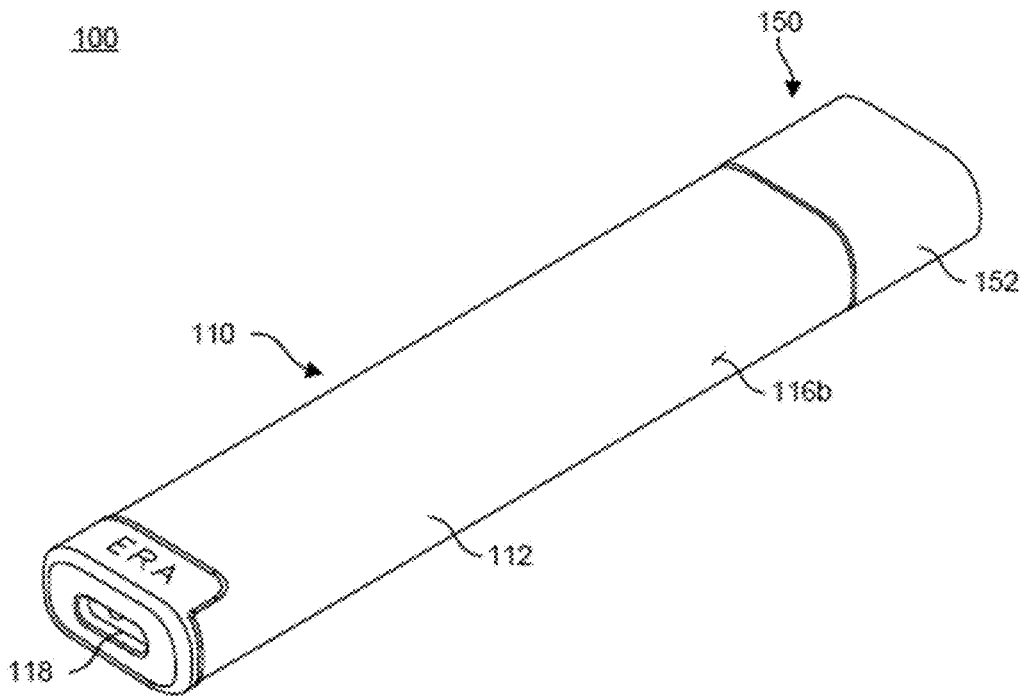
Figure 1F:
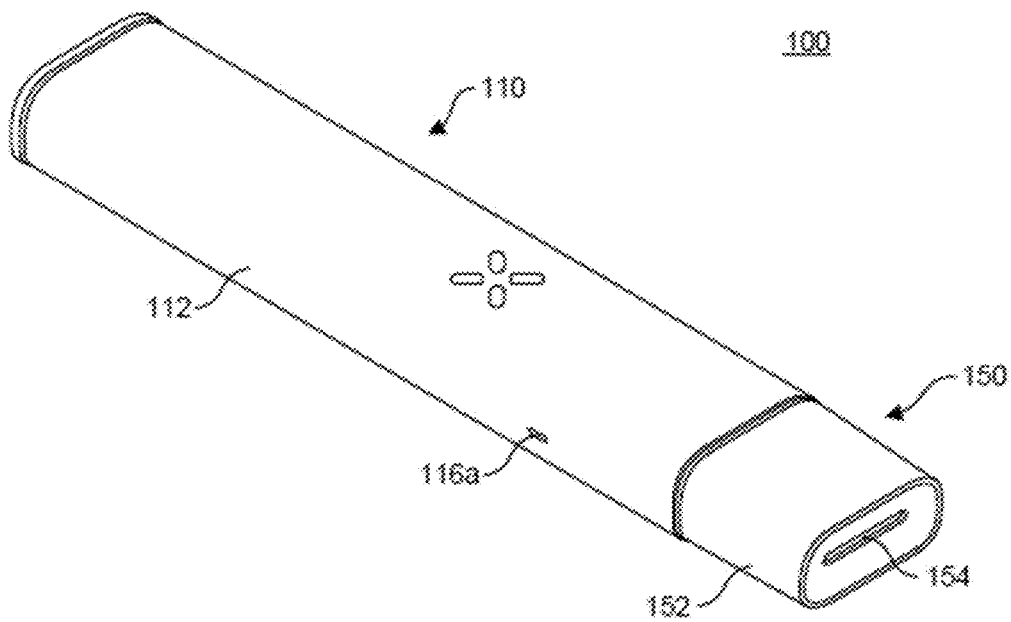

FIG. 1A-FIG. 1F illustrates features of a vaporizer device 100 including a vaporizer body 110 and a cartridge 150 consistent with implementations of the current subject matter. FIG. 1A is a bottom perspective view, and FIG. 1B is a top perspective view of the vaporizer device 100 with the cartridge 150 separated from a cartridge receptacle 114 on the vaporizer body 110. Both of the views in FIG. 1A and FIG. 1B are shown looking towards a mouthpiece 152 of the cartridge 150. FIG. 1C is a bottom perspective view, and FIG. 1D is a top perspective view of the vaporizer device with the cartridge 150 separated from the cartridge receptacle 114 of the vaporizer body 110. FIG. 1C and FIG. 1D are shown looking toward the distal end of the vaporizer body 110. FIG. 1E is top perspective view, and FIG. 1F is a bottom perspective view of the vaporizer device 100 with the cartridge 150 engaged for use with the vaporizer body 110.

As shown in FIG. 1A-FIG. 1D, the cartridge 150 includes, at the proximal end, a mouthpiece 152 that is attached over a cartridge body 156 that forms a reservoir or tank 158 that holds a vaporizable material. The cartridge body 156 may be transparent, translucent, opaque, or a combination thereof. The mouthpiece 152 may include one or more openings 154 (see FIG. 1A, FIG. 1B, FIG. 1F) at the proximal end out of which vapor may be inhaled, by drawing breath through the vaporizer device 100. The distal end of the cartridge body 156 may couple to and be secured to the vaporizer body 110 within the cartridge receptacle 114 of the vaporizer body 110. Power pin receptacles 160a,b (see FIG. 1C, FIG. 1D) of the cartridge 150 mate with respective power pins or contacts 122a,b (see, for example, FIG. 2) of the vaporizer body 110 that extend into the cartridge receptacle 114. The cartridge 150 also includes air flow inlets 162a,b on the distal end of the cartridge body 156.

A tag 164, such as a data tag, a near-field communication (NFC) tag, or other type of wireless transceiver or communication tag, may be positioned on at least a portion of the distal end of the cartridge body 156. As shown in FIG. 1C and FIG. 1D, the tag 164 may substantially surround the power pin receptacles 160a,b and the air flow inlets 162a,b, although other configurations of the tag 164 may be implemented as well. For example, the tag 164 may be positioned between the power pin receptacle 160a and the power pin receptacle 160b, or the tag 164 may be shaped as a circle, partial circle, oval, partial oval, or any polygonal shape encircling or partially encircling the power pin receptacles 160a,b and the air flow inlets 162a,b or a portion thereof.

In the example of FIG. 1A, the vaporizer body 110 has an outer shell or cover 112 that may be made of various types of materials, including for example aluminum (e.g., AL6063), stainless steel, glass, ceramic, titanium, plastic (e.g., Acrylonitrile Butadiene Styrene (ABS), Nylon, Polycarbonate (PC), Polyethersulfone (PESU), and the like), fiberglass, carbon fiber, and any hard, durable material. The proximal end of the vaporizer body 110 includes an opening forming the cartridge receptacle 114, and the distal end of the vaporizer body 110 includes a connection 118, such as, for example, a universal serial bus Type C (USB-C) connection and/or the like. The cartridge receptacle 114 portion of the vaporizer body 110 includes one or more openings (air inlets) 116a,b that extend through the outer shell 112 to allow airflow therein, as described in more detail below. The vaporizer body 110 as shown has an elongated, flattened tubular shape that is curvature-continuous, although the vaporizer body 110 is not limited to such a shape. The vaporizer body 110 may take the form of other shapes, such as, for example, a rectangular box, a cylinder, and the like.

The cartridge 150 may fit within the cartridge receptacle 114 by a friction fit, snap fit, and/or other types of secure connection. The cartridge 150 may have a rim, ridge, protrusion, and/or the like for engaging a complimentary portion of the vaporizer body 110. While fitted within the cartridge receptacle 114, the cartridge 150 may be held securely within but still allow for being easily withdrawn to remove the cartridge 150.

Although FIG. 1A-FIG. 1F illustrate a certain configuration of the vaporizer device 100, the vaporizer device 100 may take other configurations as well.

Figure 2:
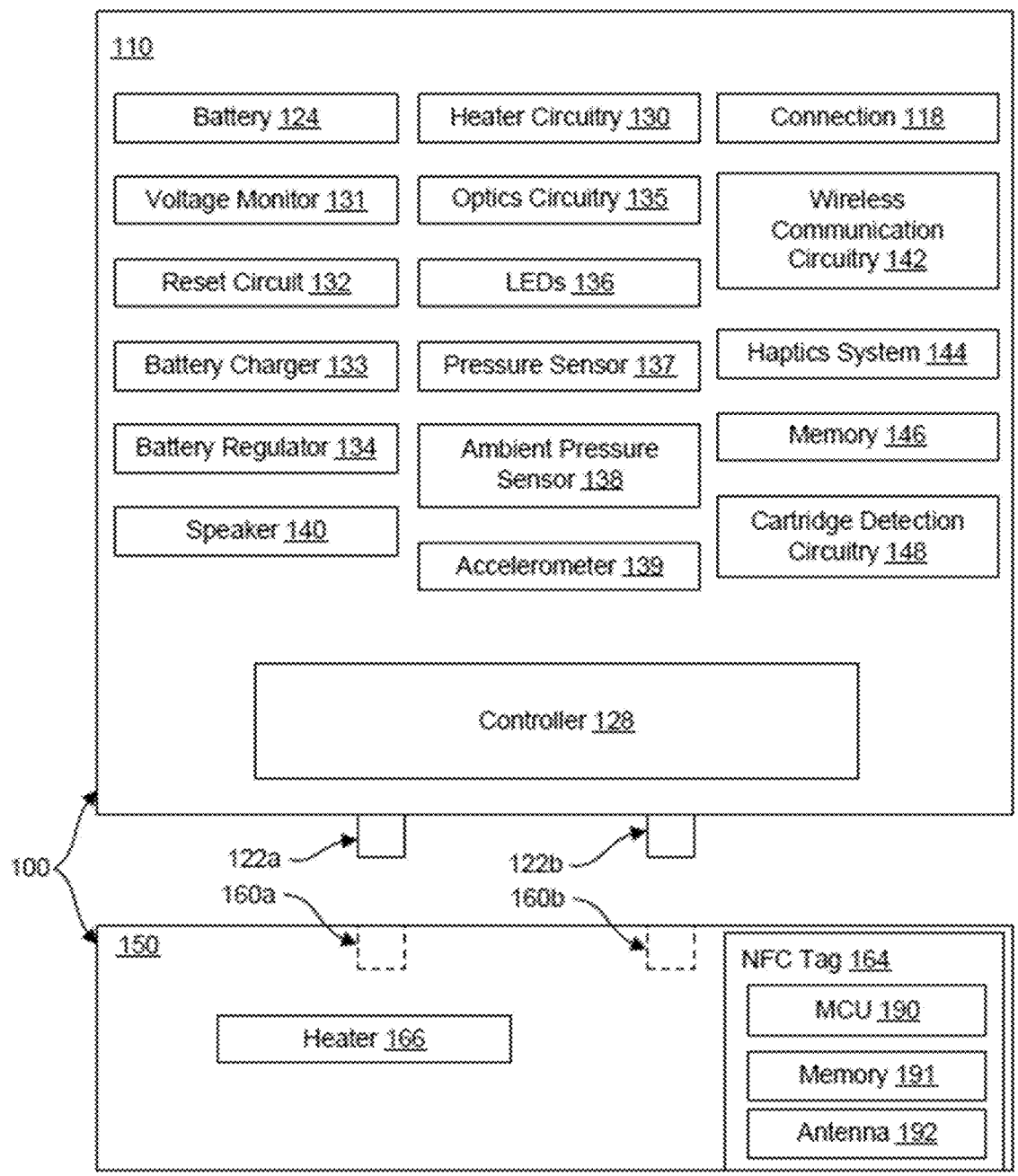
FIG. 2 is a schematic block diagram illustrating features of a vaporizer device having a cartridge and a vaporizer body consistent with implementations of the current subject matter.

FIG. 2 is a schematic block diagram illustrating components of the vaporizer device 100 having the cartridge 150 and the vaporizer body 110 consistent with implementations of the current subject matter. Included in the vaporizer body 110 is a controller 128 that includes at least one processor and/or at least one memory configured to control and manage various operations among the components of the vaporizer device 100 described herein.

Heater control circuitry 130 of the vaporizer body 110 controls a heater 166 of the cartridge 150. The heater 166 may generate heat to provide vaporization of the vaporizable material. For example, the heater 166 may include a heating coil (e.g., a resistive heater) in thermal contact with a wick which absorbs the vaporizable material, as described in further detail below.

A battery 124 is included in the vaporizer body 110, and the controller 128 may control and/or communicate with a voltage monitor 131 which includes circuitry configured to monitor the battery voltage, a reset circuit 132 configured to reset (e.g., shut down the vaporizer device 100 and/or restart the vaporizer device 100 in a certain state), a battery charger 133, and a battery regulator 134 (which may regulate the battery output, regulate charging/discharging of the battery, and provide alerts to indicate when the battery charge is low, etc.).

The power pins 122a,b of the vaporizer body 110 engage the complementary power pin receptacles 160a,b of the cartridge 150 when the cartridge 150 is engaged with the vaporizer body 110. Alternatively, power pins may be part of the cartridge 150 for engaging complementary power pin receptacles of the vaporizer body 110. The engagement allows for the transfer of energy from an internal power source (e.g., the battery 124) to the heater 166 in the cartridge 150. The controller 128 may regulate the power flow (e.g., an amount or current and/or a voltage amount) to control a temperature at which the heater 166 heats the vaporizable material contained in the reservoir 158. According to implementations of the current subject matter, a variety of electrical connectors other than a pogo-pin and complementary pin receptacle configuration may be used to electrically connect the vaporizer body 110 and the cartridge 150, such as for example, a plug and socket connector.

The controller 128 may control and/or communicate with optics circuitry 135 (which controls and/or communicates with one or more displays such as LEDs 136 which may provide user interface output indications), a pressure sensor 137, an ambient pressure sensor 138, an accelerometer 139, and/or a speaker 140 configured to generate sound or other feedback to a user.

The pressure sensor 137 may be configured to sense a user drawing (e.g., inhaling) on the mouthpiece 152 and activate the heater control circuitry 130 of the vaporizer body 110 to accordingly control the heater 166 of the cartridge 150. In this way, the amount of current supplied to the heater 166 may be varied according the user's draw (e.g., additional current may be supplied during a draw, but reduced when there is not a draw taking place). The ambient pressure sensor 138 may be included for atmospheric reference to reduce sensitivity to ambient pressure changes and may be utilized to reduce false positives potentially detected by the pressure sensor 137 when measuring draws from the mouthpiece 152.

The accelerometer 139 (and/or other motion sensors, capacitive sensors, flow sensors, strain gauge(s), or the like) may be used to detect user handling and interaction, for example, to detect movement of the vaporizer body 110 (such as, for example, tapping, rolling, and/or any other deliberate movement associated with the vaporizer body 110).

The vaporizer body 110, as shown in FIG. 2, includes wireless communication circuity 142 that is connected to and/or controlled by the controller 128. The wireless communication circuity 142 may include a near-field communication (NFC) antenna that is configured to read from and/or write to the tag 164 of the cartridge 150. Alternatively or additionally, the wireless communication circuity 142 may be configured to automatically detect the cartridge 150 as it is being inserted into the vaporizer body 110. In some implementations, data exchanges between the vaporizer body 110 and the cartridge 150 take place over NFC. In some implementations, data exchanges between the vaporizer body 110 and the cartridge 150 may take place via a wired connection such as various wired data protocols.

The wireless communication circuitry 142 may include additional components including circuitry for other communication technology modes, such as Bluetooth circuitry, Bluetooth Low Energy circuitry, Wi-Fi circuitry, cellular (e.g., LTE, 4G, and/or 5G) circuitry, and associated circuitry (e.g., control circuitry), for communication with other devices. For example, the vaporizer body 110 may be configured to wirelessly communicate with a remote processor (e.g., a smartphone, a tablet, a computer, wearable electronics, a cloud server, and/or processor based devices) through the wireless communication circuitry 142, and the vaporizer body 110 may through this communication receive information including control information (e.g., for setting temperature, resetting a dose counter, etc.) from and/or transmit output information (e.g., dose information, operational information, error information, temperature setting information, charge/battery information, etc.) to one or more of the remote processors.

The tag 164 may be a type of wireless transceiver and may include a microcontroller unit (MCU) 190, a memory 191, and an antenna 192 (e.g., an NFC antenna) to perform the various functionalities described below with further reference to FIG. 3. The tag 164 may be, for example, a 1 Kbit or a 2 Kbit NFC tag that is of type ISO/IEC 15693. NFC tags with other specifications may also be used. The tag 164 may be implemented as active NFC, enabling reading and/or writing information via NFC with other NFC compatible devices including a remote processor, another vaporizer device, and/or wireless communication circuitry 142. Alternatively, the tag 164 may be implemented using passive NFC technology, in which case other NFC compatible devices (e.g., a remote processor, another vaporizer device, and/or wireless communication circuitry 142) may only be able to read information from the tag 164.

The vaporizer body 110 may include a haptics system 144, such as an actuator, a linear resonant actuator (LRA), an eccentric rotating mass (ERM) motor, or the like that provide haptic feedback such as a vibration as a "find my device" feature or as a control or other type of user feedback signal. For example, using an app running on a user device (such as, for example, a user device 305 shown in FIG. 3), a user may indicate that he/she cannot locate his/her vaporizer device 100. Through communication via the wireless communication circuitry 142, the controller 128 sends a signal to the haptics system 144, instructing the haptics system 144 to provide haptic feedback (e.g., a vibration). The controller 128 may additionally or alternatively provide a signal to the speaker 140 to emit a sound or series of sounds. The haptics system 144 and/or speaker 140 may also provide control and usage feedback to the user of the vaporizer device 100; for example, providing haptic and/or audio feedback when a particular amount of a vaporizable material has been used or when a period of time since last use has elapsed. Alternatively or additionally, haptic and/or audio feedback may be provided as a user cycles through various settings of the vaporizer device 100. Alternatively or additionally, the haptics system 144 and/or speaker 140 may signal when a certain amount of battery power is left (e.g., a low battery warning and recharge needed warning) and/or when a certain amount of vaporizable material remains (e.g., a low vaporizable material warning and/or time to replace the cartridge 150). Alternatively or additionally, the haptics system 144 and/or speaker 140 may also provide usage feedback and/or control of the configuration of the vaporizer device 100 (e.g., allowing the change of a configuration, such as target heating rate, heating rate, etc.).

The vaporizer body 110 may include circuitry for sensing/detecting when a cartridge 150 is connected and/or removed from the vaporizer body 110. For example, cartridge-detection circuitry 148 may determine when the cartridge 150 is connected to the vaporizer body 110 based on an electrical state of the power pins 122a,b within the cartridge receptacle 114. For example, when the cartridge 150 is present, there may be a certain voltage, current, and/or resistance associated with the power pins 122a,b, when compared to when the cartridge 150 is not present. Alternatively or additionally, the tag 164 may also be used to detect when the cartridge 150 is connected to the vaporizer body 110.

The vaporizer body 110 also includes the connection (e.g., USB-C connection, micro-USB connection, and/or other types of connectors) 118 for coupling the vaporizer body 110 to a charger to enable charging the internal battery 124. Alternatively or additionally, electrical inductive charging (also referred to as wireless charging) may be used, in which case the vaporizer body 110 would include inductive charging circuitry to enable charging. The connection 118 at FIG. 2 may also be used for a data connection between a computing device and the controller 128, which may facilitate development activities such as, for example, programming and debugging, for example.

The vaporizer body 110 may also include a memory 146 that is part of the controller 128 or is in communication with the controller 128. The memory 146 may include volatile and/or non-volatile memory or provide data storage. In some implementations, the memory 146 may include 8 Mbit of flash memory, although the memory is not limited to this and other types of memory may be implemented as well.

In operation, after the vaporizer device 100 is charged, a user may activate the vaporizer device 100 by drawing (e.g., inhaling) through the mouthpiece. The vaporizer device 100 may detect a draw (e.g., using a pressure sensor, flow sensors, and/or the like, including a sensor configured to detect a change in temperature or power applied to a heater element) and may increase the power to a predetermined temperature preset. The power may be regulated by the controller by detecting the change in resistance of the heating coil and using the temperature coefficient of resistivity to determine the temperature.

In accordance with some implementations of the current subject matter, the vaporizer device 100 may be controlled so that the temperature used to vaporize the vaporizable material is maintained within a preset range. In general, the controller may control the temperature of the resistive heater (e.g., resistive coil, etc.) based on a change in resistance due to temperature (e.g., temperature coefficient of resistance (TCR)). For example, a heater may be any appropriate resistive heater, such as, for example, a resistive coil. The heater is typically coupled to the heater controller via two or more connectors (electrically conductive wires or lines) so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater.

Figure 3:
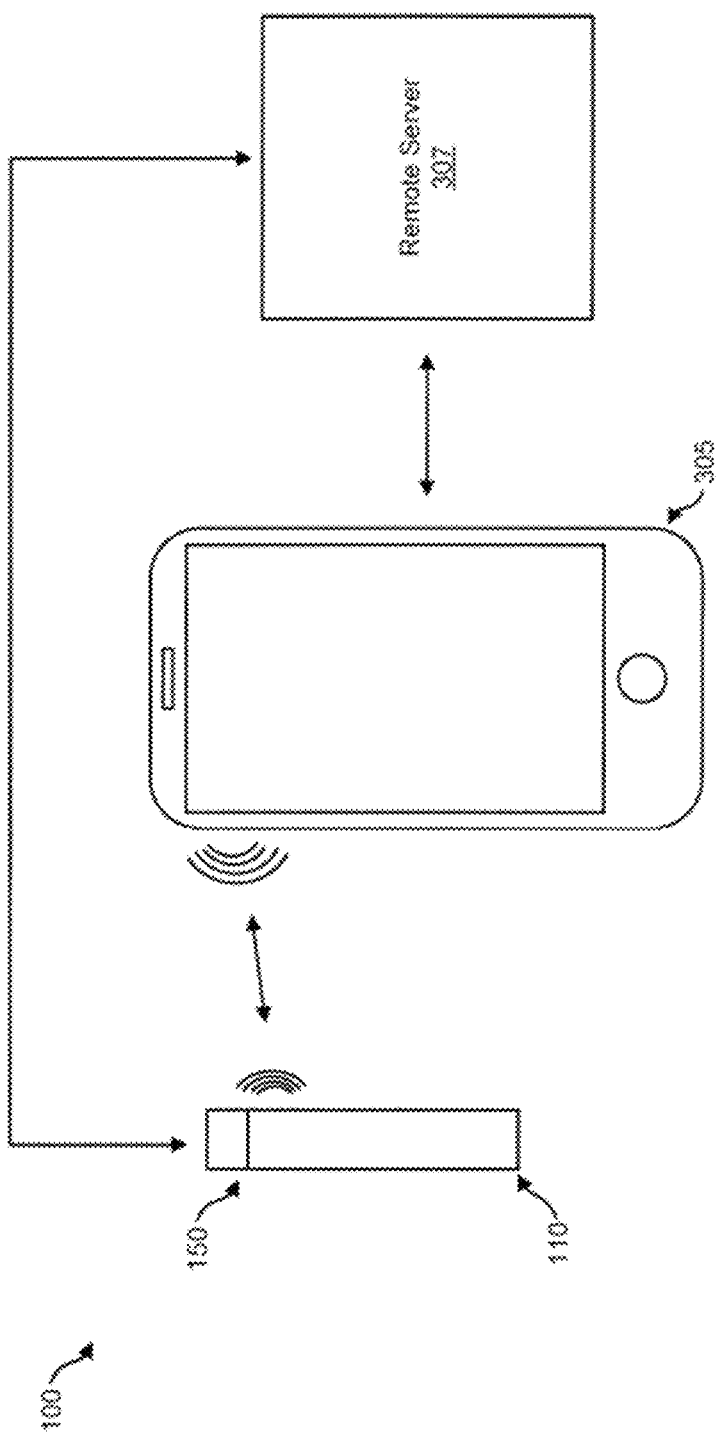
FIG. 3 illustrates communication between a vaporizer device, a user device, and a server consistent with implementations of the current subject matter.

FIG. 3 illustrates communication between the vaporizer device 100 (including the vaporizer body 110 and the cartridge 150), the user device 305 (e.g., a smartphone, tablet, laptop, desktop computer, a workstation, and/or the like), and a remote server 307 (e.g., a server coupled to a network, a cloud server coupled to the Internet, and/or the like) consistent with implementations of the current subject matter. The user device 305 wirelessly communicates with the vaporizer device 100. A remote server 307 may communicate directly with the vaporizer device 100 or through the user device 305. The vaporizer body 110 may communicate with the user device 305 and/or the remote server 307 through the wireless communication circuitry 142. In some implementations, the cartridge 150 may establish through the tag 164 communication with the vaporizer body 110, the user device 305, and/or the remote server 307. While the user device 305 in FIG. 3 is depicted as a type of handheld mobile device, the user device 305 consistent with implementations of the current subject matter is not so limited and may be, as indicated, various other types of user computing devices.

An application software ("app") running on at least one of the remote processors (the user device 305 and/or the remote server 307) may be configured to control operational aspects of the vaporizer device 100 and receive information relating to operation of the vaporizer device 100. For example, the app may provide a user with capabilities to input or set desired properties or effects, such as, for example, a particular temperature or desired dose, which is then communicated to the controller 128 of the vaporizer body 110 through the wireless communication circuitry 142. The app may also provide a user with functionality to select one or more sets of suggested properties or effects that may be based on the particular type of vaporizable material in the cartridge 150. For example, the app may allow adjusting heating based on the type of vaporizable material, the user's (of the vaporizer device 100) preferences or desired experience, and/or the like. The app may be a mobile app and/or a browser-based or web app. For example, the functionality of the app may be accessible through one or more web browsers running on one or more types of user computing devices.

Data read from the tag 164 from the wireless communication circuitry 142 of the vaporizer body 110 may be transferred to one or more of the remote processors (e.g., the user device 305 and/or the remote server 307) to which it is connected, which allows for the app running on the one or more processors to access and utilize the read data for a variety of purposes. For example, the read data relating to the cartridge 150 may be used for providing recommended temperatures, dose control, usage tracking, and/or assembly information.

The cartridge 150 may also communicate directly, through the tag 164, with other devices. This enables data relating to the cartridge 150 to be written to/read from the tag 164, without interfacing with the vaporizer body 110. The tag 164 thus allows for identifying information (e.g., pod ID, batch ID, etc.) related to the cartridge 150 to be associated with the cartridge 150 by one or more remote processors. For example, when the cartridge 150 is filled with a certain type of vaporizable material, this information may be transmitted to the tag 164 by filling equipment. Then, the vaporizer body 110 is able to obtain this information from the tag 164 (e.g., via the wireless communication circuity 142 at the vaporizer body 110) to identify the vaporizable material currently being used and accordingly adjust the controller 128 based on, for example, user-defined criteria or pre-set parameters associated with the particular type of vaporizable material (set by a manufacturer or as determined based upon user experiences/feedback aggregated from other users). For example, a user may establish (via the app) a set of criteria relating to desired effects for or usage of one or more types of vaporizable materials. When a certain vaporizable material is identified, based on communication via the tag 164, the controller 128 may accordingly adopt the established set of criteria, which may include, for example, temperature and dose, for that particular vaporizable material.

As described above, the vaporizer device 100 and/or the user device 305 that is part of a vaporizer system as defined above may include a user interface (e.g., including an app or application software) that may be executed on the user device 305 in communication, which may be configured to determine, display, enforce, and/or meter dosing.

The vaporizer device 100 consistent with implementations of the current subject matter may be configured to facilitate social interaction through the vaporizer device 100. For example, the vaporizer device 100 may be configured to share usage information with others, such as third parties including health care providers, etc., for better prescription and administration of medical treatment. The vaporizer device 100 may also be configured to communicate with non-medical third parties (e.g., friends, colleagues, etc.), and with unknown third parties (making some or all information publically available). In some implementations, the vaporizer device 100 described herein, either by itself or in communication with one or more communications devices that are part of a system, may identify and provide information about the operation, status, or user input from the vaporizer device 100 to a public or private network.

Software, firmware, or hardware that is separate or separable from the vaporizer device and that wirelessly communicates with the vaporizer device 100 may be provided as described with respect to FIG. 3. For example, applications ("apps") may be executed on a processor of a desktop device or station and/or a portable and/or wearable device, including smartphones, smartwatches, and the like, which may be referred to as a personal digital device, a user device, or optionally just a device (e.g., user device 305 in FIG. 3) that is part of a connected system. The user device 305 may provide an interface for the user to engage and interact with functions related to the vaporizer device 100, including communication of data to and from the vaporizer device 100 to the user device 305 and/or additional third party processor (e.g., servers such as the remote server 307 in FIG. 3). For example, a user may control some aspects of the vaporizer device 100 (temperature, session size, etc.) and/or data transmission and data receiving to and from the vaporizer device 100, optionally over a wireless communication channel between first communication hardware of the user device 305 and second communication hardware of the vaporizer device 100. Data may be communicated in response to one or more actions of the user (e.g., including interactions with a user interface displayed on the user device 305), and/or as a background operation such that the user does not have to initiate or authorize the data communication process.

User interfaces may be deployed on the user device 305 and may aid the user in operating the vaporizer device 100. For example, the user interface operating on the user device 305 may include icons and text elements that may inform the user of various ways that settings may be adjusted or configured by the user. In this manner (or in others consistent with the current subject matter) information about the vaporizer device 100 may be presented using a user interface displayed by the user device 305. Icons and/or text elements may be provided to allow the user to see information regarding one or more statuses of the vaporizer device 100, such as battery information (charge remaining, draws remaining, time to charge, charging, etc.), cartridge status (e.g., type of cartridge and vaporizable material, fill status of cartridge, etc.), and other device statuses or information. Icons and/or text elements may be provided to allow the user to update internal software (a.k.a., firmware) in the vaporizer device 100. Icons and text elements may be provided to allow the user to set security and/or authorization features of the vaporizer device 100, such as setting a PIN code to activate the vaporizer device 100 or the use of personal biometric information as a way of authentication. Icons and text elements may be provided to allow the user to configure foreground data sharing and related settings.

The vaporizer device 100 may perform onboard data gathering, data analysis, and/or data transmission methods. As mentioned, the vaporizer device 100 having wired or wireless communication capability may interface with digital consumer technology products such as smart phones, tablet computers, laptop/netbook/desktop computers, wearable wireless technologies such as "smart watches," and other wearable technology such as Google "Glass," or similar through the use of programming, software, firmware, GUI, wireless communication, wired communication, and/or software commonly referred to as application(s) or "apps." A wired communication connection may be used to interface the vaporizer device 100 to digital consumer technology products for the purpose of the transmission and exchange of data to/from the vaporizer device from/to the digital consumer technology products (and thereby also interfacing with apps running on the digital consumer technology products). A wireless communication connection may be used to interface the vaporizer device 100 to digital consumer technology products for the transmission and exchange of data to/from the vaporizer device 100 from/to the digital wireless interface. The vaporizer device may use a wireless interface that includes one or more of an infrared (IR) transmitter, a Bluetooth interface, an 802.11 specified interface, and/or communications with a cellular telephone network in order to communicate with consumer technology.

Consistent with implementations of the current subject matter, the vaporizable material used with the vaporizer device may be provided within the cartridge. The vaporizer device may be a cartridge-using vaporizer device, a cartridge-less vaporizer device, or a multi-use vaporizer device capable of use with or without a cartridge. For example, a multi-use vaporizer device may include a heating chamber (e.g., an oven) configured to receive the vaporizable material directly in the heating chamber and also configured to receive the cartridge having a reservoir or the like for holding the vaporizable material. In various implementations, the vaporizer device may be configured for use with liquid vaporizable material (e.g., a carrier solution in which an active and/or inactive ingredient(s) are suspended or held in solution or a liquid form of the vaporizable material itself) or solid vaporizable material. Solid vaporizable material may include a plant material that emits some part of the plant material as the vaporizable material (e.g., such that some part of the plant material remains as waste after the vaporizable material is emitted for inhalation by a user) or optionally may be a solid form of the vaporizable material itself such that all of the solid material may eventually be vaporized for inhalation. Liquid vaporizable material may likewise be capable of being completely vaporized or may include some part of the liquid material that remains after all of the material suitable for inhalation has been consumed.

Aspects of the current subject matter relating to delivering to a user a fixed amount of aerosol by a vaporizer device are not limited to use with the particular and/or exact configurations and/or components of the vaporizer device 100, the vaporizer body 110, and the cartridge 150 described with reference to FIG. 1A-FIG. 3. Rather, the foregoing descriptions are provided as examples in which the described aspects may be utilized. Variations of the example vaporizer devices described herein may be used with aspects of the current subject matter directed to delivering to a user a fixed amount of aerosol. For example, in one implementation, a single-use integrated vaporizer device, which may not include a removable cartridge, may employ the aspects of delivering a fixed amount of aerosol consistent with implementations of the current subject matter. Aspects of the current subject matter may be employed with various other vaporizer devices, vaporizer bodies, and cartridges and/or with various modifications of the vaporizer device 100, the vaporizer body 110, and the cartridge 150 described herein. For example, consistent with implementations of the current subject matter, various sensors and circuitry may not be required for the operations provided herein. For example, the ambient pressure sensor 138, the accelerometer 139, and/or the cartridge detection circuitry 148 may not be required in some implementations. Various other combinations of configurations and/or components of the vaporizer device 100, the vaporizer body 110, and the cartridge 150 may be employed consistent with implementations of the current subject matter.

Additionally, while some implementations of the current subject matter may be described with respect to cannabis and cannabinoid-based vaporizable materials, for example cannabis oils, the disclosure is not limited to cannabis and cannabinoid-based vaporizable materials and may be applicable to other types of materials.

Turning to aspects of delivering to a user a fixed amount of aerosol (e.g., a fixed dose or a dose), the user may wish to control an amount of aerosol consumed (e.g., inhaled) and/or may wish to track and monitor the amount of aerosol consumed or the number of doses consumed. Aspects of the current subject matter are directed to delivering to the user a fixed amount of aerosol, which, according to implementations described herein, may be represented by a dose and/or a dose size. According to aspects of the current subject matter, a dose is defined as a fixed amount of aerosol generated by the vaporizer device 100 for consumption by the user as a number of puffs taken by the user until the fixed amount of aerosol is consumed or inhaled. According to some implementations of the current subject matter, once the fixed amount of aerosol is consumed or inhaled, the vaporizer device 100 may stop or pause operation (e.g., by stopping production of aerosol through control of the heater 166).

In particular, aspects of the current subject matter provide for using data mapped to (e.g., stored on) the tag 164 (or other wireless transceiver or tag) of the cartridge 150 or otherwise associated with the cartridge 150 to identify an amount of aerosol (e.g., reflected as a dose size) to be generated. The controller 128 utilizes the mapped data to appropriately control generation of the aerosol. The mapped data may include factors relevant to the generation of the aerosol in the fixed amount (e.g., data indicative of the fixed amount of aerosol), as discussed further herein. Some implementations of the current subject matter allow for the user to, for example, select a particular cartridge 150 that is indicated to deliver a fixed or preselected amount of aerosol. Other implementations of the current subject matter allow for the user to activate or otherwise select and/or enable dose control settings in which a dose size may be selected and associated with the cartridge 150. In some implementations, the user may adjust the fixed or preselected amount of aerosol (e.g., the dose size). In this way, the user is made aware of and chooses the desired amount of aerosol to be consumed. By user selection of the particular cartridge 150 or adjustment of the fixed or preselected amount of aerosol that is mapped to provide the fixed amount of aerosol in the dose size, implementations of the current subject matter provide for the vaporizer device 100 to automatically control the amount of aerosol generated without additional user interactions.

According to aspects of the current subject matter, data related to the fixed or preselected amount of aerosol may be persisted at the cartridge 150 such that the data is mapped and retained to the cartridge 150, allowing for the settings to be ported between different vaporizer devices and, in some instances, remain enabled until disabled by the user.

In some implementations, in addition to the fixed dose size associated with the cartridge 150, the cartridge 150 may have a maximum number of doses associated with the cartridge 150. During use of the vaporizer device 100 by the user, the data mapped to the tag 164 may be updated to allow for determinations of percent of vaporizable material used, percent of vaporizable material remaining, and other metrics related to use of the cartridge 150 as further described herein.

Consistent with implementations of the current subject matter, the fixed amount of aerosol to be delivered to the user may be based on an amount of energy used to produce vapor from the vaporizable material. In some implementations, the amount of energy is a fixed amount. In some implementations, the amount of energy may be one factor in combination with additional factors to determine the fixed amount of aerosol to be delivered to the user. The additional factors may include, for example, a preset or predetermined temperature for the dose, characteristics or properties of the vaporizable material (such as viscosity, age or date of production, chemical composition, concentrations, etc.), and/or usage data (such as date of production of the cartridge 150, frequency of use of the cartridge 150, date and time of last use of the cartridge 150, number of doses completed, etc.). Various fixed amounts (e.g., dose sizes) may be defined such that the fixed amount of aerosol corresponds to an amount of energy to be sent to the heater 166. Once the defined amount of energy is reached, energy supply to the heater 166 may, in some implementations, be temporarily cut off. Thus, the fixed dose sizes are applied by limiting the amount of energy supplied to the heater 166 to result in a controlled amount of vapor being produced from the vaporizable material.

Consistent with some implementations of the current subject matter, the data mapped to the tag 164 for delivering a fixed amount of aerosol may include, for example, a total or sum of energy consumed value, a fixed dose cartridge identifier, a dose size (e.g., an amount of energy to achieve one dose), a target maximum energy value, a cartridge lock identifier, a number of doses consumed value, a dose size setting, a target maximum number of doses, a dose control setting, and/or a last dose time and date stamp. The data mapped to the tag 164 may be provided in various combinations, and each of type of data may not be required for delivering a fixed amount of aerosol, as further described herein.

Consistent with some implementations of the current subject matter, the data may be obtained from the tag 164 by the wireless communication circuitry 142 and provided to the controller 128 to control the amount of energy sent to the heater 166 to provide for the fixed amount of aerosol to be delivered. The data mapped to the tag 164 may in some instances be modifiable by the user. The data mapped to the tag 164 may be updated after a dose for subsequent doses and/or other uses. Other data may be stored on the tag 164 to further enhance the delivery of the fixed amount of aerosol consistent with implementations provided herein. Moreover, as previously described, other data stored on the tag 164 may be used for other purposes and operations.

In accordance with additional aspects of the current subject matter, a cartridge identifier may be stored on the tag 164 or other wireless transceiver or tag of the cartridge 150. The controller 128 may obtain and use the cartridge identifier to query the remote server 307 (e.g., a database) to obtain the data necessary for delivering a fixed amount of aerosol for the cartridge 150. The cartridge identifier and associated data may be stored on the remote server 307 and accessible to the controller 128 through for example the wireless communication circuitry 142. The controller 128 may provide updated data related to the use of the cartridge 150 to the remote server 307 for updating and modifying usage data, which may be used by the controller 128 in subsequent operations as further described herein.

The total (or sum of) energy consumed value mapped to the tag 164 (or otherwise associated with the cartridge 150) is a function of the fixed or selected dose size associated with the cartridge 150 (which may be user modifiable as further described herein) and the number of doses used for the cartridge 150. For example, an unused cartridge 150 has a value of zero for the total energy consumed. Each time the cartridge 150 is used, the value of the total energy consumed is increased relative to the amount of energy supplied to achieve the particular dose size. For example, for a dose size corresponding to 1,000 micro-Joules (mJ), for each dose the total energy consumed is increased by 1,000 mJ. In some instances, the user may not complete a full dose, in which case the total energy consumed may be a portion of that of the full dose size (e.g., 500 mJ). The portion or partial amount of the energy consumed is used as the value of the total energy consumed for a particular dose. Consistent with implementations of the current subject matter, during use of the cartridge 150, the controller 128 monitors the amount of energy supplied and accordingly updates the total energy consumed value. The total energy consumed value is thus not user-modifiable as it is based on use of the cartridge 150.

The fixed dose cartridge identifier mapped to the tag 164 (or otherwise associated with the cartridge 150) is, according to some implementations, a value or identifier that indicates if a fixed dose is associated with the cartridge 150. For example, a binary value of "1" may represent that the cartridge 150 is a fixed dose cartridge, while a value of "0" may represent that the cartridge 150 is not a fixed dose cartridge. Other, non-binary values or identifiers may be used to identify the cartridge 150 as a fixed dose cartridge. Upon activation of the vaporizer device 100, the controller 128 may check the value of the fixed dose identifier to determine if operation of the vaporizer device 100 should be consistent with fixed dose parameters. The value of the fixed dose cartridge identifier may be initially set by a manufacturer of the cartridge 150, where the manufacturer may include an entity that makes or produces the cartridge 150, an entity that supplies the vaporizable material, an entity that fills the vaporizable material into the cartridge 150, or a combination thereof. In some instances, the value of the fixed dose cartridge identifier is not user-modifiable. In other instances, the user may override or otherwise change the value of the fixed dose cartridge identifier via, for example, options provided on the app running on the user device 305. For example, the user may decide that he or she does not want to utilize the fixed dose features and may thus change the settings via the app.

The dose control setting is, according to some implementations, a value or identifier that indicates if dose control settings are activated for the particular cartridge 150. A value of "1" may represent that dose control is activated, while a value of "0" may represent that dose control is not activated. The dose control setting is, in some implementations, the same as or equivalent to the fixed dose cartridge identifier. In some implementations, both the dose control setting and the fixed dose cartridge identifier may be used. For example, the fixed dose cartridge identifier may signify that there are a fixed number of doses associated with the cartridge 150, while the dose control setting may signify if a particular dose control setting is set to, for example, limit the number of doses for a particular period of time. The controller 128 may check the value of the dose control setting 607 to determine if operation of the vaporizer device 100 should be consistent with dose control parameters. The value of the dose control setting 607 may be initially set by a manufacturer of the cartridge 150, where the manufacturer may include an entity that makes or produces the cartridge 150, an entity that supplies the vaporizable material, an entity that fills the vaporizable material into the cartridge 150, or a combination thereof. In some instances, the value of the dose control setting 607 is not user-modifiable. In other instances, the user may override or otherwise change the value of the dose control setting 607 via, for example, options provided on the app running on the user device 305. For example, the user may decide that he or she does not want to utilize the dose control settings and may thus change the settings via the app.

The dose size (e.g., amount of aerosol to be consumed) value mapped to the tag 164 (or otherwise associated with the cartridge 150) is a numeric value that indicates the amount of energy supplied to achieve the particular dose size. For example, the dose size value may be a number of mJ per dose. The dose size value serves as an input to signify to the controller 128 the amount of energy to supply to the heater 166 for a dose. In some implementations, the amount of energy may be one factor in combination with additional factors to determine the fixed amount of aerosol to be delivered to the user. The additional factors may contribute to aerosol production. In some instances, the value of the dose size may be a default value that is initially set by the manufacturer. In some instances, the value of the dose size is not user-modifiable. In other instances, the user may override or otherwise change the value of the dose size via, for example, options provided on the app running on the user device 305. For example, the user may decide that he or she prefers a smaller amount or a larger amount of aerosol to be delivered during a dose and may thus change the dose size via the app. In some instances, the user may change the value of the dose size by selecting a preconfigured option, for example micro, small, medium, or large. In some instances, rather than selecting a preconfigured option, the user may change the value of the dose size by indicating an amount or value deviating from the preset dose size; for example, 3 times greater the current preset dose size, ½ the current preset dose size, etc. This may be convenient as it allows for a user not to be required to know an amount in terms of energy but rather in general terms of size of a dose. For example, the preconfigured options may signify in general terms how much vapor is being produced for inhalation by the user during a given dose. Other descriptive terms or identifiers (e.g., symbols, numbers, and the like) may also be used for dose sizes, and the implementations described herein are not limited to the specific terms of micro, small, medium, and large describing the dose size.

The dose size setting represents the number of doses selected or otherwise indicated for the vaporizer device 100 to generate for consumption. The dose size setting may be initially set and associated with the cartridge 150 (e.g., by an entity that makes or produces the cartridge 150, an entity that supplies the vaporizable material, an entity that fills the vaporizable material into the cartridge 150, or a combination thereof), and/or the dose size setting may be user configurable and/or adjustable.

The target maximum energy value mapped to the tag 164 (or otherwise associated with the cartridge 150) may be a constant value (e.g., it does not change during use of the vaporizer device 100) that signifies an amount of energy that may be applied to the heater 166 until the cartridge may stop functioning (e.g., the vaporizable material is depleted). In some implementations, when the maximum energy value is reached, the cartridge 150 may stop functioning. In some implementations, the maximum energy value is used with the total energy consumed value as a comparison to determine how much energy remains for doses in the cartridge 150; this may serve as a type of fuel gauge for the user. Consistent with implementations of the current subject matter, the maximum energy value may be based on total particulate matter, which refers to the amount of vaporizable material removed from the cartridge 150 (e.g., from a wicking element of the heater 166) by vaporization or aerosolization and suspended in the vapor for consumption by the user. For example, there is a correlation between the amount of energy supplied and an amount of vaporizable material removed from the cartridge 150. With this knowledge, the maximum energy value for the cartridge 150 may be determined. In some instances, the maximum energy value may be initially set by a manufacturer of the cartridge 150 and is not user-modifiable. In some implementations, the tag 164 may be tagged with a specific amount of energy and/or other parameters to be controlled by the vaporizer device 100. In some implementations, the tag 164 may be tagged with a target number of doses to be consumed. Based on the target number of doses, the controller 128 or a remote processor may adjust the amount of energy and/or other parameters to achieve the target number of doses. For example, the energy to achieve the target number of doses may vary based on parameters such as setpoint temperature (e.g., when the vaporizer device 100 is set at different temperatures, the total energy needed to produce a target total particulate matter, on which the target number of doses is based, may differ).

The cartridge lock identifier mapped to the tag 164 (or otherwise associated with the cartridge 150) is, according to some implementations, a value or identifier that indicates to the vaporizer device 100 whether the cartridge 150 may be activated. For example, binary values may be used where a value of "1" may represent that the cartridge 150 is locked and cannot be used, while a value of "0" may represent that the cartridge 150 is not locked and may be used. The controller 128 may check the value of the cartridge lock identifier to determine if the controller 128 should apply energy to the heater 166. A default setting of the cartridge lock identifier may be initially set to, for example "1" but may be changed to "0" by the controller 128 upon a determination that, for example, a maximum number of doses associated with the cartridge 150 has not been reached. In some instances, the cartridge lock identifier is not user-modifiable. In other instances, the user may override or otherwise change the cartridge lock identifier via, for example, options provided on the app running on the user device 305. For example, the user may decide to lock the cartridge 150 so that it cannot be used. In other implementations, the cartridge 150 may be locked for safety, compliance, and/or legal reasons. For example, a signal may be remotely sent via the app, the user device 305, and/or the remote server 307 to initiate a lock by changing the cartridge lock identifier mapped to the tag 164 (or otherwise associated with the cartridge 150) to a value or identifier indicative of a lock such that the controller 128 reads the cartridge lock identifier and responds by not applying energy to the heater 166. The reasons for locking a cartridge 150 may include, but are not limited to, a voluntary recall of a batch of the vaporizable material; geographical location to ensure compliance with local law; and/or an age verification feature to ensure that the user is of legal age to consume the vaporizable material.

The number of dose consumed value mapped to the tag 164 (or otherwise associated with the cartridge 150) is a numeric value that is increased after each dose to record usage of the cartridge 150. For example, the total number of dose used value increments by one upon completion of each dose. In an implementation of the current subject matter, the vaporizer device 100 may update the tag 164 with the number of doses completed (e.g., adding "dose size setting" value to a prior number of doses). In an alternate implementation, a processor, such as a remote processor at the user device 305 or at the remote server 307, may analyze data generated by the vaporizer device 100 and may revise the number of doses consumed value based on measurements recorded during use (e.g., during one or more puffs). For example, measurements of puff duration, puff volume, setpoint temperature, ambient temperature, and/or ambient pressure may affect the number of doses consumed, which may affect amount of vaporizable material remaining and other use data. The number of doses consumed as adjusted based on the measurements may be less than or greater than a number of doses nominally consumed.

The target maximum number of doses may be used to provide data related to number of doses remaining in the cartridge 150, also serving as a type of fuel gauge for the user.

A last dose time and date stamp may be mapped to the tag 164 or otherwise associated with the cartridge 150. This data may be used to provide usage information to the user and/or to the remote server 307 for usage analysis. Additionally, in some implementations, the time and date stamp may be used by the vaporizer device 100 to time a temporary timeout period. When activated for subsequent doses, the vaporizer device 100 may check the time and date stamp to identify the time and date of the last completed dose and may compare this to a predefined timeout period to determine when another dose may be initiated. In some implementations, the timeout period may be user configurable and/or user adjustable. In some implementations, the timeout period is established and associated with the cartridge 150 and/or the vaporizer device 100.

With reference to FIG. 4A-FIG. 4E, a series of data 410-450 mapped to the tag 164 of the cartridge 150, or otherwise associated with the cartridge 150, is provided consistent with implementations of the current subject matter. The series of data 410-450 in the examples of FIG. 4A-FIG. 4E includes values for the following data types: a total energy consumed 401, a fixed dose cartridge identifier 402, a dose size 403, a target maximum energy 404, a cartridge lock identifier 405, and a total number of doses consumed 406. The data may, in some implementations, may be associated with the cartridge 150 by a cartridge identifier and accessible to the controller 128. The data included in the examples provided are not limiting and are provided for example only. Additional data may be included, such as additional factors in combination with the amount of energy to determine the fixed amount of aerosol to be delivered to the user (e.g., a preset or predetermined temperature for the dose, characteristics or properties of the vaporizable material (such as viscosity, age or date of production, chemical composition, concentrations, etc.), and/or usage data (such as date of production of the cartridge 150, frequency of use of the cartridge 150, date and time of last use of the cartridge 150, number of doses completed, etc.)). Some data types, for example the fixed dose cartridge identifier 402 and/or the cartridge lock identifier 405, may not be needed in some implementations.

In FIG. 4A, the series of data 410 is representative of a new, unused cartridge 150. The total energy consumed 401 is 0; the fixed dose cartridge identifier 402 is "1" signifying that the cartridge 150 is a fixed dose cartridge; the dose size 403 is 1,000 mJ, which represents the number of mJ per dose and serves as an input to signify to the controller 128 the amount of energy to supply to the heater 166 for a dose; the maximum energy 404 is 300,000 mJ, which represents the amount of energy that may applied to the heater 166 until the cartridge 150 stops functioning; the cartridge lock identifier 405 is "0" signifying that the cartridge 150 is not locked and may be used; and the total number of doses used 406 is 0. The amount 1,000 mJ representing an energy required per dose is one example of an energy value that may be used. Doses are not limited to a particular energy value. Additionally, consistent with implementations of the current subject matter, the energy value may be adjusted based on other parameters, such as setpoint temperature (e.g., the temperature set for vaporization). The maximum energy value, or target maximum energy value, of 300,000 mJ is also an example value based on, for example, the particular cartridge 150 and an amount and/or type of the vaporizable material contained therein.

Consistent with implementations of the current subject matter, while a user device 305 is not required for the fixed dose and/or dose control cartridge features described herein, the user may nevertheless utilize an app running on the user device 305, which may result in a display of features relevant to the fixed dose and/or dose control cartridge and use thereof being provided. For example, data such as number of doses used, percentage of the cartridge 150 depleted, and the dose size may be displayed. With respect to the series of data 410, the number of doses used is 0, the percent of the cartridge 150 depleted is 0%, and the dose size may be a preconfigured identifier associated with 1,000 mJ, for example "small." Such data may be displayed on a user interface of the user device 305.

In FIG. 4B, the series of data 420 is representative of a first dose of the cartridge 150. The total energy consumed 401 is 1,000 mJ; the fixed dose cartridge identifier 402 is "1"; the dose size 403 is 1,000 mJ; the target maximum energy 404 is 300,000; the cartridge lock identifier 405 is "0"; and the total number of doses used 406 is 1. Data displayed on the user device 305 may now indicate, for example, that the percent of vaporizable material of the cartridge 150 depleted is 0.3% (e.g., 1,000/300,000).

In FIG. 4C, the series of data 430 of the cartridge 150 is representative of the user increasing the default dose size after five doses of the cartridge 150. The total energy consumed 401 is 5,000 mJ; the fixed dose cartridge identifier 402 is "1"; the dose size 403 is adjusted to 4,000 mJ; the target maximum energy 404 is 300,000; the cartridge lock identifier 405 is "0"; and the total number of doses used 406 is 5. Data displayed on the user device 305 may now indicate that the number of doses used is 5, the percent of the cartridge 150 depleted is 1.6% (e.g., 5,000/300,000), and the dose size is, for example, a custom dose size.

In FIG. 4D, the series of data 440 of the cartridge 150 is representative of the user completing one dose with the custom dose size. The total energy consumed 401 is 9,000 mJ (4,000 mJ+5,000 mJ); the fixed dose cartridge identifier 402 is "1"; the dose size 403 is 4,000 mJ; the target maximum energy 404 is 300,000; the cartridge lock identifier 405 is "0"; and the total number of doses used 406 is 6. Data displayed on the user device 305 may now indicate that the number of doses used is 6, the percent of the cartridge 150 depleted is 3% (e.g., 9,000/300,000), and the dose size is a custom dose size.

In FIG. 4E, the series of data 450 of the cartridge 150 is representative of the user reaching the maximum energy value of 300,000 mJ. The total energy consumed 401 is 301,000 mJ; the fixed dose cartridge identifier 402 is "1"; the dose size 403 is 4,000 mJ; the maximum energy 404 is 300,000; the cartridge lock identifier 405 is changed to "1" to signify that the cartridge 150 is now locked and cannot be used; and the total number of doses used 406 is 80. Data displayed on the user device 305 may now indicate that the number of doses used is 80, the percent of the cartridge 150 depleted is 100%, and the dose size is a custom dose size.

The series of data 410-450 are purely exemplary and non-limiting, intended to demonstrate how data mapped to the tag 164 is used for the fixed dose cartridge features according to aspects of the current subject matter.

Figure 5:
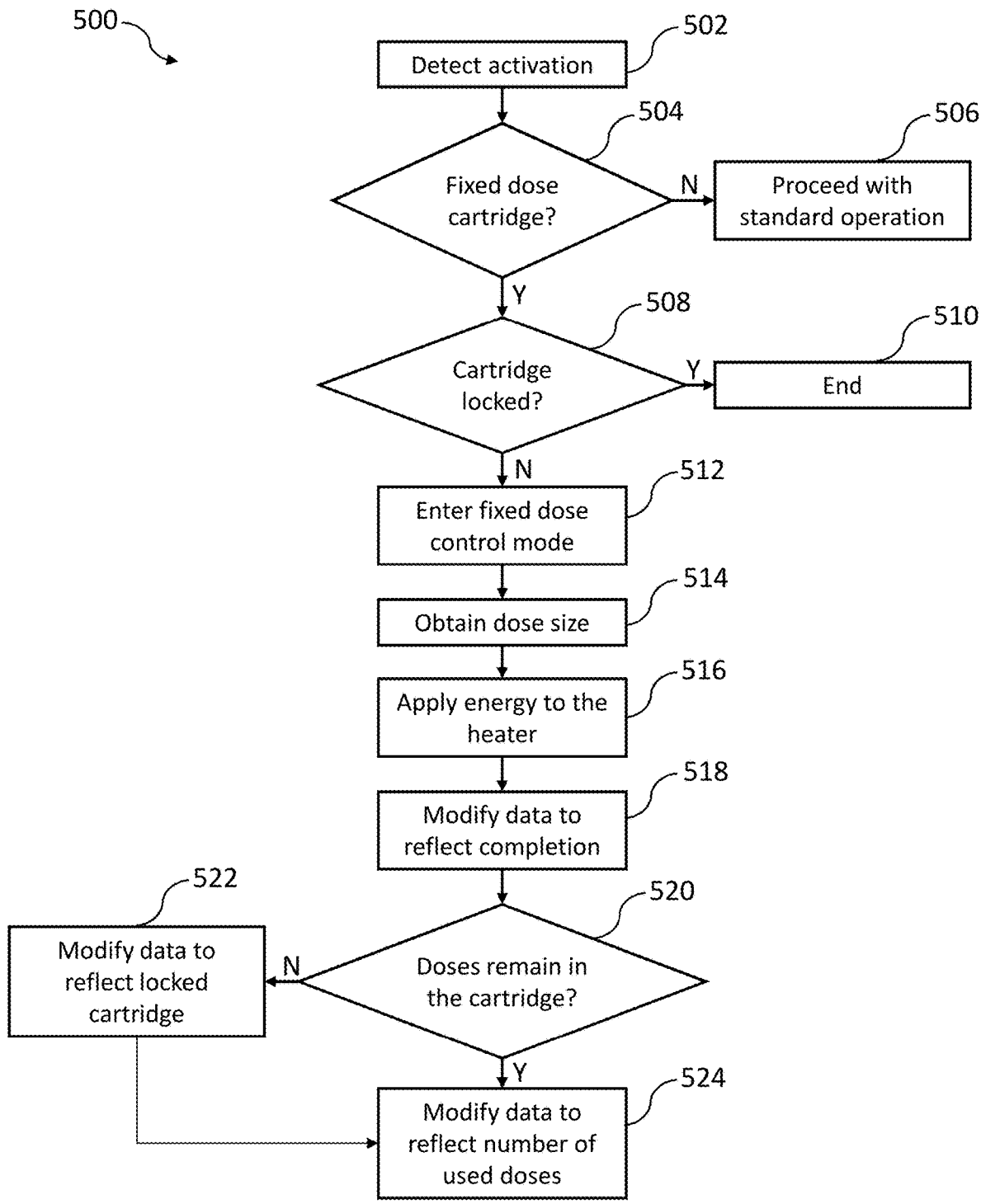
FIG. 5 shows a process flow chart illustrating features of a method consistent with some example implementations of the current subject matter.

FIG. 5 depicts a flowchart illustrating a process 500 for operating the vaporizer device 100 consistent with implementations of the current subject matter. In some example embodiments, the vaporizer device 100, for example, the controller 128, may perform the process 500 to implement fixed dose features of the cartridge 150.

At 502, the vaporizer device 100 may detect activation of the vaporizer device 100 by a user. For example, the vaporizer device 100 may detect that the cartridge 150 is present in the cartridge receptacle 114 on the vaporizer body 110 of the vaporizer device 100 and/or may detect a user puff on the mouthpiece 152 of the vaporizer device 100. In some instances, one or more output signals from the heater control circuitry 130 to the controller 128 may indicate whether the cartridge 150 is present in or absent from the cartridge receptacle 114 in the vaporizer body 110 of the vaporizer device 100. In some instances, puff detection may be based on signals to the controller 128 from the pressure sensor 137 and/or the ambient pressure sensor 138. In some instances, other forms of puff detection may be utilized such as capacitance sensing and/or microphone implementations. In some implementations, activation of the vaporizer device 100 may be determined by other signals, such as signals indicative of movement of the vaporizer device 100.

At 504, the vaporizer device 100 may determine if the cartridge 150 is a fixed dose cartridge. For example, the controller 128 may query the data mapped to the tag 164 to determine if the value of the fixed dose cartridge identifier 402 is a value that indicates a fixed dose is associated with the cartridge 150 (e.g., a value of "1"). Thus, in some implementations, upon activation of the vaporizer device 100, the controller 128 may check the value of the fixed dose identifier 402 to determine if operation of the vaporizer device 100 should be consistent with fixed dose parameters.

At 506, if the value of the fixed dose identifier 402 indicates that the cartridge 150 does not have fixed dose parameters associated with the cartridge or that the fixed dose parameters are not enabled, the controller 128 may proceed with standard operation of the vaporizer device 100.

At 508, if the value of the fixed dose identifier 402 indicates that the cartridge 150 does have fixed dose parameters associated with the cartridge 150 or that the fixed dose parameters are enabled, the vaporizer device 100 determines whether the cartridge 150 is locked. For example, the controller 128 may query the data mapped to the tag 164 to determine if the value of the cartridge lock identifier 405 is a value that indicates that the cartridge 150 is in a locked state and should not be used, or if the value of the cartridge lock identifier 405 is a value that indicates that the cartridge 150 is not locked and may be used. In some implementations, 508 and the determination of whether the cartridge is locked may be bypassed or not included as part of the process 500.

At 510, if the value of the cartridge lock identifier 405 indicates that the cartridge 150 is locked, the controller 128 does not proceed with controlling operation of the vaporizer device 100 and the process ends.

At 512, if on the other hand the value of the cartridge lock identifier 405 indicates that the cartridge 150 is not locked, the vaporizer device 100 proceeds by entering a fixed dose control mode. Features of the fixed dose control mode may include the following operations consistent with implementations of the current subject matter.

At 514, the vaporizer device 100 obtains a dose size associated with the cartridge 150. For example, the controller 128 may query the mapped data of the tag 164 to obtain a value of the dose size 403. The value of the dose size 403 may be a numeric value that indicates the amount of energy to be applied to achieve the particular dose size. For example, the dose size value may be a number of mJ per dose. The value of the dose size 403 serves as an input to signify to the controller 128 the amount of energy to supply to the heater 166 for a dose.

At 516, the vaporizer device 100 applies to the heater 166 the amount of energy needed to achieve the dose size associated with the cartridge 150. For example, the controller 128 may apply to a heating element of the heater 166 the amount of energy signified by the value of the dose size 403.

At 518, following the dose in which the required amount of energy is applied to the heating element for the dose size associated with the cartridge 150, the vaporizer device 100 may modify the data to reflect completion of the dose. For example, the controller 128 may modify the value of the total energy consumed 401 to reflect the energy applied during the dose. The value of the total energy consumed 401 may be used to determine the percentage of the cartridge 150 that is depleted, which may be valuable or of interest to the user. The value of the total energy consumed 401 is also used to determine if any doses remain in the cartridge 150.

At 520, the vaporizer device 100 determines if any doses remain in the cartridge 150. For example, the controller 128 may compare the value of the total energy consumed 401 with the value of the maximum energy 404. If the total energy consumed 401 is greater than or equal to the value of the maximum energy 404, in some implementations no doses remain available in the cartridge 150. In some implementations, if the total energy consumed 401 is greater than or equal to the value of the maximum energy 404, the cartridge 150 may continue to function. If, on the other hand, the total energy consumed 401 is less than the maximum energy 404, this serves as an indication to the controller 128 that additional doses remain available in the cartridge 150.

At 522, if it is determined at 520 that no doses remain in the cartridge 150, the vaporizer device 100 may in some implementations accordingly modify the data mapped to the tag 164 to reflect that the cartridge 150 should be locked. For example, the controller 128 may modify the value of the cartridge lock identifier 405 to signify that the cartridge 150 is now locked and cannot be used. As previously described, the cartridge locked aspects may be bypassed or not included in the process 500.

At 524, following the determination at 520 that doses remain in the cartridge 150 and following the modification at 524 of the data mapped to the tag 164, the vaporizer device 100 may modify the data to reflect the number of doses used to date. For example, the controller 128 may increment the value of the total number of doses used 406. This data may be, for example, displayed to the user.

According to additional implementations of the current subject matter, dose control settings may be enabled to provide for the vaporizer device 100 to generate a number of doses based on a selected dose size. Consistent with implementations of the current subject matter, the dose control settings may be persistent to the cartridge 150 such that the dose control settings are mapped and retained to the cartridge 150, allowing for the dose control settings to be ported between different vaporizer devices and, in some instances, remain enabled until disabled by the user.

With reference to FIG. 6, a diagram 600 includes a series of data 610-650 mapped to the tag 164 of the cartridge 150, or otherwise associated with the cartridge 150, consistent with implementations of the current subject matter. The series of data 610-650 in the example of FIG. 6 includes values for the following data types: a total energy consumed value 601, a number of doses consumed value 602, a dose size setting 603, a dose size value 604, a target maximum energy value 605, a target number of doses 606, a dose control setting 607, and a last dose time/date stamp 608. The data may, in some implementations, may be associated with the cartridge 150 by a cartridge identifier and accessible to the controller 128. In some implementations, a cartridge identifier is not necessary. The data included in the example provided are not limiting and are provided for example only. Additional data may be included, such as additional factors in combination with the amount of dose energy to provide the dose including the fixed amount of aerosol to be delivered to the user (e.g., a preset or predetermined temperature for the dose, characteristics or properties of the vaporizable material (such as viscosity, age or date of production, chemical composition, concentrations, etc.), and/or usage data (such as date of production of the cartridge 150, frequency of use of the cartridge 150, date and time of last use of the cartridge 150, number of doses completed, etc.)). Some data types, for example the last dose time/date stamp 608, may not be needed in some implementations.

With continued reference to FIG. 6 and referring to the series of data 610-650 mapped to the tag 164 of the cartridge 150, provided is an example use case of dose control settings consistent with implementations of the current subject matter. The data 610 is representative of the cartridge 150 being set for dose control (e.g., the dose control setting 607 set to "1") but not yet used (e.g., the total energy consumed value 601 and the number of doses consumed value 602 are 0).

The data 620 is representative of a first dose being taken and/or consumed, as the total energy consumed value 601 is 1,000 mJ and is equal to the dose size value 604. The number of doses consumed value is incremented to 1.

The data 630 is representative of the dose size setting value 603 changed to 4, and 4 doses consumed. The total energy consumed value 601 is 5,000 mJ, and the number of doses consumed value 602 is incremented to 5.

The data 640 is representative of the second dose size of 4 being consumed. The total energy consumed value 601 is 9,000 mJ, and the number of doses consumed value 602 is incremented to 9.

The data 650 is representative of the cartridge 150 being depleted. The number of doses consumed value 602 is 502 and exceeds the target maximum number of doses 606 set at 500. Similarly, the total energy consumed value 601 exceeds the target maximum energy value 605 (502,000 mJ and 500,000 mJ, respectively). The number of doses consumed and the total energy consumed may be higher than their respective targets due to less energy being needed per dose, which may be determined by measurements recorded during use (e.g., during one or more puffs). For example, as described herein, measurements of puff duration, puff volume, ambient temperature, and/or ambient pressure may affect the number of doses consumed, which may affect amount of vaporizable material remaining and other use data. The number of doses consumed as adjusted based on the measurements may be less than or greater than a number of doses nominally consumed. As shown by the data 650, the number of doses consumed in the example is greater than the number of doses nominally consumed (e.g., based on energy values alone).

Figure 7:
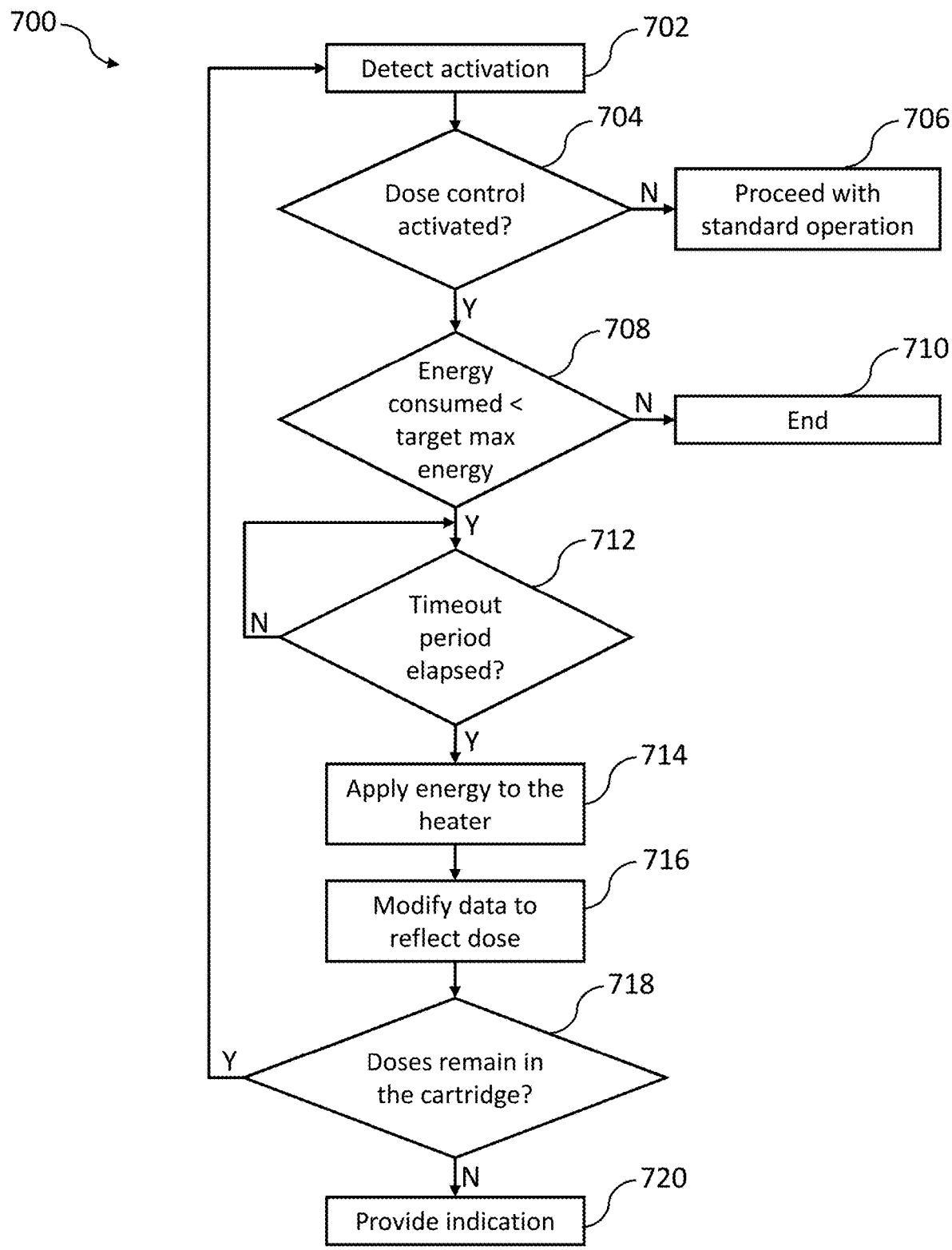
FIG. 7 shows a process flow chart illustrating features of a method consistent with implementations of the current subject matter.

FIG. 7 depicts a flowchart illustrating a process 700 for operating the vaporizer device 100 consistent with dose control implementations of the current subject matter. In some example embodiments, the vaporizer device 100, for example, the controller 128, may perform the process 600 to implement dose control features associated with the cartridge 150.

At 702, the vaporizer device 100 may detect activation of the vaporizer device 100 by a user. For example, the vaporizer device 100 may detect that the cartridge 150 is present in the cartridge receptacle 114 on the vaporizer body 110 of the vaporizer device 100 and/or may detect a user puff on the mouthpiece 152 of the vaporizer device 100. In some instances, one or more output signals from the heater control circuitry 130 to the controller 128 may indicate whether the cartridge 150 is present in or absent from the cartridge receptacle 114 in the vaporizer body 110 of the vaporizer device 100. In some instances, puff detection may be based on signals to the controller 128 from the pressure sensor 137 and/or the ambient pressure sensor 138. In some instances, other forms of puff detection may be utilized such as capacitance sensing and/or microphone implementations. In some implementations, activation of the vaporizer device 100 may be determined by other signals, such as signals indicative of movement of the vaporizer device 100.

At 704, the vaporizer device 100 may determine if dose control settings are activated for the cartridge 150. For example, the controller 128 may query the data mapped to the tag 164 to determine if the value of the dose control setting 607 is a value that indicates dose control is activated for the cartridge 150 (e.g., a value of "1"). Thus, in some implementations, upon activation of the vaporizer device 100, the controller 128 may check the value of the dose control setting 607 to determine if operation of the vaporizer device 100 should be consistent with parameters established for dose control.

At 706, if the value of the dose control setting 607 indicates that the cartridge 150 does not have dose control settings activated, the controller 128 may proceed with standard operation of the vaporizer device 100.

At 708, if the value of the dose control setting 607 indicates that dose control settings are activated for the cartridge 150, the vaporizer device 100 determines whether the total energy consumed value 601 is less than the target maximum energy value 605. This determination may be made to, for example, determine if doses remain in the cartridge 150. For example, the controller 128 may query the data mapped to the tag 164 to compare the energy values 601 and 605. In some implementations, operation 708 and the determination related to the comparison of the energy values to determine if doses remain in the cartridge 150 may be bypassed and/or not included as part of the process 700.

At 710, if the determination at 708 indicates that the total energy consumed value is greater than or equal to the target maximum energy value, the controller 128 does not proceed with controlling operation of the vaporizer device 100 and the process ends.

At 712, if on the other hand the determination at 708 indicates that the total energy consumed value is less than the target maximum energy value, a subsequent determination may be made as to if a timeout period has elapsed. For example, the vaporizer device 100 may compare the time and date stamp 608 to the current time and date to determine if a predefined timeout period has elapsed. This comparison may be done to, for example, ensure that a new dose is not being started before expiration of the timeout period. If the timeout period has not elapsed, the process 700 may continue to check the time and date stamp 608 against the current time and date until the timeout period has elapsed.

At 714, upon a determination that the timeout period has elapsed, the vaporizer device 100 applies to the heater 166 the amount of energy needed to achieve the dose size associated with the cartridge 150. For example, the controller 128 may apply to a heating element of the heater 166 the amount of energy signified by the value of the dose size 604.

At 716 following the completion of the dose during which the required amount of energy is applied to the heater 166 for the dose size associated with the cartridge 150, the vaporizer device 100 may modify the data to reflect completion of the dose. For example, the controller 128 may modify the value of the total energy consumed 601 to reflect the energy applied during the dose and the value of the number of doses consumed 602. The value of the total energy consumed 601 may be used to determine the percentage of the cartridge 150 that is depleted, which may be valuable or of interest to the user. The value of the total energy consumed 601 and/or the number of doses consumed 602 may also be used to determine if any doses remain in the cartridge 150. The time and date stamp 608 may also be modified to reflect the time and date at which the dose was completed.

At 718, the vaporizer device 100 may determine if any doses remain in the cartridge 150. For example, the controller 128 may compare the value of the total energy consumed 601 with the value of the target maximum energy 605. If the total energy consumed 601 is greater than or equal to the value of the target maximum energy 605, in some implementations, no doses remain available in the cartridge 150.

At 720, if it is determined at 718 that no doses remain in the cartridge 150, the vaporizer device 100 may in some implementations provide an indication to alert the user. For example, the vaporizer device 100 may generate feedback in the form of haptics, audio, or visual alerts. The vaporizer device 100 may transmit to the user device 305 a signal to indicate completion of the cartridge 150. The user device 305 may accordingly update the user via the app in a notification, for example.

If it is determined at 718 that doses remain in the cartridge 150, the process 700 may resume at 702 to detect activation and implement the dose control process consistent with implementations of the current subject matter.

As described elsewhere herein, the app running on at least one of the remote processors (the user device 305 and/or the remote server 307) may be configured to control operational aspects of the vaporizer device 100 and receive information relating to operation of the vaporizer device 100. For example, in some implementations, the app may provide to the remote server 307 and/or the user device 305 information related to the vaporizer device 100.

In particular, consistent with implementations of the current subject matter, the app may provide for display to the user device 305 information related to the fixed dose capabilities, features, and parameters of the cartridge 150. For example, a user interface of the user device 305 may include an indication that the cartridge 150 is a fixed dose cartridge and/or that dose control settings are activated or established, and may additionally include related features and parameters. For example, by comparing the value of the total energy consumed 401 and the value of the target maximum energy 404 in the tag 164 mapped data, a percentage of the cartridge 150 remaining and a number of doses remaining at the fixed dose size (e.g., using value of the dose size 403) may be determined and displayed. The energy values (e.g., the total energy consumed 401 and the maximum energy 404) may also be utilized with other data, for example data relating to consumption behaviors of the user (e.g., frequency of use, date of first use, etc.), to determine and display other parameters such as an estimate of how long the cartridge 150 will last.

The app utilizing the data mapped to the tag 164 may also provide for generation and display of usage information, including a history of use of the cartridge 150, a total number of doses consumed to date (e.g., the value of the number of doses consumed 602), an average dose size (by comparing a value of the total energy consumed 401 with a value of the total number of doses consumed 406), and/or the like. Usage information may also include data related to doses consumed with various user devices 305.

As noted, the app running on at least one of the remote processors (the user device 305 and/or the remote server 307) allows for the user to control operational aspects of the vaporizer device 100 and the fixed dose capabilities and parameters of the cartridge 150. For example, the app may allow the user to modify the dose size 403 and/or the dose size setting 603. The user may select a preconfigured dose size, such as micro, small, medium, or large, or the user may set a custom size setting. The user may select a dose size such as a numerical value.

Consistent with additional implementations of the current subject matter, additional factors may be taken into account to refine the repeatability of the dose size, and improve uniformity of total particulate matter across cartridges with differing contents and differing consumption contexts. For example, in addition to the total particulate matter (which as described is used in the determination of the amount of energy to apply to the heater to achieve vaporization or aerosolization of the vaporizable material), other factors including the chemical composition of the vaporizable material, temperature and other ambient conditions, viscosity of the vaporizable material, usage history of the cartridge 150 (date of production, frequency of use, date and time of last use, etc.), characteristics of the heater (e.g., properties of a wick and of a heating element), and/or the like may be used to determine an amount of aerosol generated by the vaporizer device 100, which may be correlated to dose size and the amount of energy to apply to the heater to achieve the determined amount of aerosol.

As described elsewhere herein, the amount of energy may be one factor in combination with additional factors to determine the fixed amount of aerosol to be delivered to the user. The additional factors may include, for example, a preset or predetermined temperature for the dose, characteristics or properties of the vaporizable material (such as viscosity, age or date of production, chemical composition, concentrations, etc.), and/or usage data (such as date of production of the cartridge 150, frequency of use of the cartridge 150, date and time of last use of the cartridge 150, number of doses completed, etc.). Various fixed amounts (e.g., dose sizes) may be defined such that the fixed amount of aerosol corresponds to an amount of energy to be sent to the heater 166. Once the defined amount of energy is reached, energy supply to the heater 166 may temporarily be cut off. Thus, the fixed dose sizes are applied by limiting the amount of energy supplied to the heater 166 to result in a controlled amount of vapor being produced from the vaporizable material.

The additional factors that may be taken into account to refine the dose size of the cartridge 150 may also be used in allowing the user to modify or select configurations and parameters. For example, the user may select an option to replicate a previous dose from a different cartridge 150. Taking into account the various factors that may affect dose size, the vaporizer device 100 may replicate doses.

A visual indication of the status of the dose may be provided to the user via the app. For example, a status or progress bar indicating a completed percentage of the dose may be displayed and continuously updated (e.g., progress is updated live while puffing). The progress bar may be indicative of the amount of power supplied to the heating element and may be a representation indicating amount of vaporizable material inhaled.

According to some aspects, once the dose is completed, the vaporizer device 100 may be locked for a preset amount of time referred to as the timeout period, which may be for example 30 seconds or any desired time period. The timeout period may be user or system defined. During such a timeout period, user puffing does not produce any aerosol. Feedback may be provided to the user during the timeout period to signify that the vaporizer device 100 is locked. For example, such feedback may include visual feedback (e.g., flashing lights on the vaporizer device 100 or a visual indicator on the app) or haptic (e.g., vibration) feedback of the vaporizer device 100. Once the timeout period ends, the dose size 403, 604 and/or the dose size setting 603 may remain as the default unless otherwise updated by the user. There may be an option to overrule or end the timeout period.

After completion of the dose, it may be desirable to control the start of a new dose. In some aspects, the user may wish to limit or monitor the dose for a given time period (e.g., doses per hour, day, week, month, etc.). In order to clearly distinguish vaporizer doses from one another, the vaporizer device 100 and/or the user device 305 may require a specific user input, wait time between doses, device setting or status, or other criteria before starting a new dose.

Figure 8:
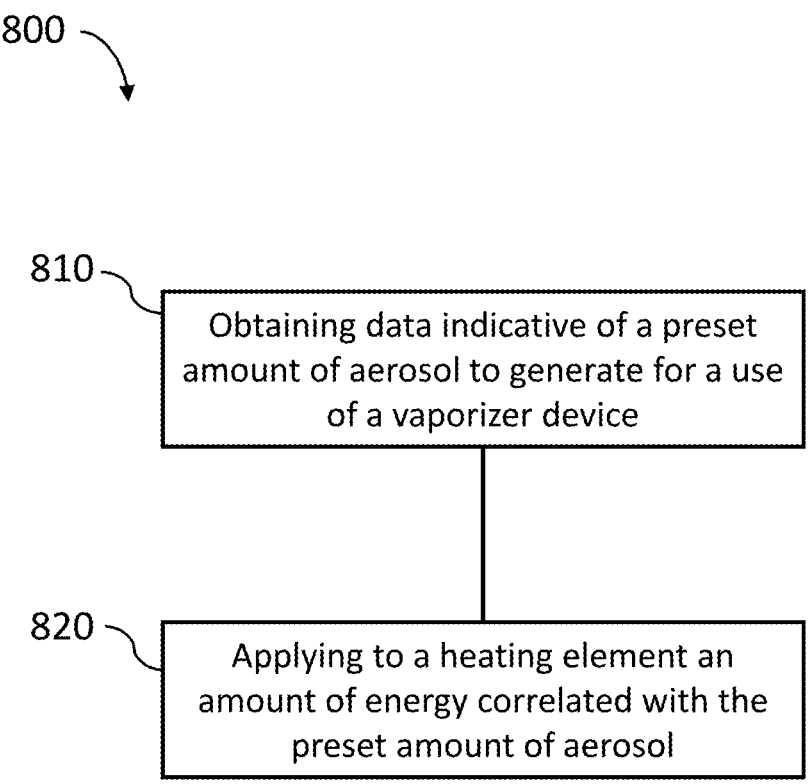
FIG. 8 shows a process flow chart illustrating features of a method consistent with additional example implementations of the current subject matter.

FIG. 8 depicts a flowchart illustrating a process 800 for operating the vaporizer device 100 consistent with implementations of the current subject matter. In some example embodiments, the vaporizer device 100, for example, the controller 128, may perform the process 800 to implement fixed dose features of the cartridge 150.

At 810, a controller 128 of a vaporizer device 100 obtains data indicative of a preset amount of aerosol to generate for use of the vaporizer device 100. For example, the data indicative of the preset amount of aerosol may include a value of the amount of energy to be applied to a heating element to generate the preset amount of aerosol. In some implementations, the amount of energy may be one factor in combination with additional factors to determine the fixed amount of aerosol to be delivered to the user. The additional factors may include, for example, a preset or predetermined temperature for the dose, characteristics or properties of the vaporizable material (such as viscosity, age or date of production, chemical composition, concentrations, etc.), and/or usage data (such as date of production of the cartridge 150, frequency of use of the cartridge 150, date and time of last use of the cartridge 150, number of doses completed, etc.). Moreover, the data indicative of the preset amount of aerosol may be associated with the cartridge 150. For example, the data indicative of the preset amount of aerosol may be stored on the tag 164 of the cartridge 150 and may be accessible by the controller 128.

At 820, the controller 128 of the vaporizer device 100 applies to the heater 166 in the cartridge 150 an amount of energy correlated with the preset amount of aerosol. By applying the amount of energy to the heater 166, the preset amount of aerosol is generated for consumption by the user. The user may take any number of puffs to consume or inhale the preset amount of aerosol, following which the vaporizer device 100 may discontinue applying energy to the heater 166. In some implementations, the user may end the dose without consuming the entire preset amount of aerosol. For example, the user may stop using the vaporizer device 100, may turn off the vaporizer device 100, or may provide an indication, for example via the app, that the user is ending the dose. In some implementations, the vaporizer device 100 may modify the data mapped to the tag 164 to reflect completion of the dose, whether a full amount or a partial amount is consumed. The value of the total energy consumed 401 or 601 may also be used to determine if any doses remain in the cartridge 150. For example, the controller 128 may compare the value of the total energy consumed 401, 601 with the value of the target maximum energy 404, 605. If the total energy consumed 401, 601 is greater than or equal to the value of the target maximum energy 404, 605, in some implementations no doses remain available in the cartridge 150. In some implementations, if the total energy consumed 401, 601 is greater than or equal to the value of the maximum energy 404, 605, the vaporizer device 100 may continue to function with the cartridge 150. If, on the other hand, the total energy consumed 401, 601 is less than the maximum energy 404, 605, this serves as an indication to the controller 128 that additional doses remain available in the cartridge 150. In some implementations, the controller 128 may modify the data mapped to the tag 164 to reflect that the cartridge 150 should be locked. In some implementations, the controller 128 may modify the data mapped to the tag 164 to reflect the number of doses used to date.

Aspects of the current subject matter advantageously provide for using data mapped to (e.g., stored on) the tag 164 (or other wireless transceiver or tag) of the cartridge 150 or otherwise associated with the cartridge 150 to identify an amount of aerosol (e.g., reflected as a dose size) to be generated. The controller 128 utilizes the mapped data to appropriately control generation of the aerosol. The mapped data may include factors relevant to the generation of the aerosol in the fixed amount (e.g., data indicative of the fixed amount of aerosol). Some implementations of the current subject matter allow for the user to, for example, select a particular cartridge 150 that is indicated to deliver a fixed or preselected amount of aerosol. Other implementations of the current subject matter allow for the user to activate or otherwise select and/or enable dose control settings in which a dose size may be selected and associated with the cartridge 150.

In some examples, the vaporizable material may include a viscous liquid such as, for example a cannabis oil. In some variations, the cannabis oil comprises between 0.3% and 100% cannabis oil extract. The viscous oil may include a carrier for improving vapor formation, such as, for example, propylene glycol, glycerol, medium chain triglycerides (MCT) including lauric acid, capric acid, caprylic acid, caproic acid, etc., at between 0.01% and 25% (e.g., between 0. 1% and 22%, between 1% and 20%, between 1% and 15%, and/or the like). In some variations the vapor-forming carrier is 1,3-Propanediol. A cannabis oil may include a cannabinoid or cannabinoids (natural and/or synthetic), and/ or a terpene or terpenes derived from organic materials such as for example fruits and flowers. For example, any of the vaporizable materials described herein may include one or more (e.g., a mixture of) cannabinoid including one or more of: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), Tetrahydrocannabinol, Cannabidiol (CBD), Cannabinol (CBN), Tetrahydrocannabinolic Acid (THCA), Cannabidioloc Acid (CBDA), Tetrahydrocannabivarinic Acid (THCVA), one or more Endocannabinoids (e.g., anandamide, 2-Arachidonoylglycerol, 2-Arachidonyl glyceryl ether, N-Arachidonoyl dopamine, Virodhamine, Lysophosphatidylinositol), and/or a synthetic cannabinoids such as, for example, one or more of: JWH-018, JWH-073, CP-55940, Dimethylheptylpyran, HU-210, HU-331, SR144528, WIN 55,212-2, JWH-133, Levonantradol (Nantrodolum), and AM-2201. The oil vaporization material may include one or more terpene, such as, for example, Hemiterpenes, Monoterpenes (e.g., geraniol, terpineol, limonene, myrcene, linalool, pinene, Iridoids), Sesquiterpenes (e.g., humulene, farnesenes, farnesol), Diterpenes (e.g., cafestol, kahweol, cembrene and taxadiene), Sesterterpenes, (e.g., geranylfarnesol), Triterpenes (e.g., squalene), Sesquarterpenes (e.g, ferrugicadiol and tetraprenylcurcumene), Tetraterpenes (lycopene, gamma-carotene, alpha- and beta-carotenes), Polyterpenes, and Norisoprenoids. For example, an oil vaporization material as described herein may include between 0.3-100% cannabinoids (e.g., 0.5-98%, 10-95%, 20-92%, 30-90%, 40-80%, 50-75%, 60-80%, etc.), 0-40% terpenes (e.g., 1-30%, 10-30%, 10-20%, etc.), and 0-25% carrier (e.g., medium chain triglycerides (MCT)).

In any of the oil vaporizable materials described herein (including in particular, the cannabinoid-based vaporizable materials), the viscosity may be within a predetermined range. The range may be between, at room temperature (23° C.) about 30 cP (centipoise) and 115 kcP (kilocentipoise), between 30 cP and 200 kcP, although higher viscosities and/or lower viscosities may be implemented as well. For example, the viscosity may be between 40 cP and 113 kcP at room temperature. Outside of this range, the vaporizable material may fail in some instances to wick appropriately to form a vapor as described herein. In particular, it is typically desired that the oil may be made sufficiently thin to both permit wicking at a rate that is useful with the apparatuses described herein, while also limiting leaking (e.g., viscosities below that of ~30 cP at room temperature might result in problems with leaking).

Although the disclosure, including the figures, described herein may described and/or exemplify these different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, comprising:
   determining, by a controller of a vaporizer device, that a total amount of energy consumed is less than a target maximum energy, wherein the vaporizer device comprises a cartridge configured to contain a vaporizable material, wherein the total amount of energy consumed represents a percentage of the vaporizable material that is depleted;
   obtaining, by the controller of the vaporizer device, a predetermined dose indicative of a preset amount of aerosol to generate for a single use of the vaporizer device, wherein the predetermined dose is indicative of the preset amount of aerosol associated with the cartridge and accessible to the controller, wherein the predetermined dose is defined by a preset amount of energy to be applied to generate the preset amount of aerosol;
   applying, by the controller and to a heating element in the cartridge, the preset amount of energy defining the predetermined dose to generate the preset amount of aerosol, wherein the preset amount of energy defining the predetermined dose is applied in response to the total amount of energy consumed being less than the target maximum energy;
   determining, based on determining that the total amount of energy consumed is less than the target maximum energy, whether a timeout period has elapsed following completion of the single use; and
   applying, based on determining that the timeout period has elapsed, the preset amount of energy defining another predetermined dose to generate the preset amount of aerosol,
   wherein the preset amount of aerosol is generated by heating the vaporizable material using the preset amount of energy defining the predetermined dose.

2. The method of claim 1, wherein data indicative of the preset amount of aerosol is stored on a near-field communication tag contained on at least a portion of the cartridge, wherein the controller is configured to obtain access data stored on the near-field communication tag.

3. The method of claim 1, wherein one or more of a value of the total amount of energy consumed, a fixed dose cartridge identifier, a value of dose size, a value of the target maximum energy, a cartridge lock identifier, a number of doses consumed, a dose size setting, a target number of doses, a dose control setting, and a time and date stamp are associated with the cartridge and accessible to the controller.

4. The method of claim 3, wherein the application of the preset amount of energy is based on one or more of the fixed dose cartridge identifier, the cartridge lock identifier, and the dose control setting.

5. The method of claim 3, further comprising:
   modifying, by the controller and following the application of the preset amount of energy, one or more of the value of the total amount of energy consumed, the number of doses consumed, and the time and date stamp.

6. The method of claim 3, further comprising:
   determining, by the controller and based on the value of the total amount of energy consumed and the value of the target maximum energy, a number of doses remaining in the cartridge.

7. The method of claim 6, further comprising:
   modifying, by the controller and in response to a determination of no doses remaining in the cartridge, the cartridge lock identifier.

8. The method of claim 3, further comprising:
   providing, by the controller and to a user device in communication with the controller for display on the user device, one or more of data indicative of the preset amount of aerosol, the value of the total amount of energy consumed, the fixed dose cartridge identifier, the value of dose size, the value of the target maximum energy, the cartridge lock identifier, the number of doses consumed, the dose size setting, the target number of doses, the dose control setting, and the time and date stamp.

9. The method of claim 3, wherein the time and date stamp may be used by the vaporizer device to time the timeout period.

10. The method of claim 1, wherein the preset amount of aerosol is one or more of a preconfigured amount and adjustable by a user through an application executed on a user device in communication with the controller.

11. A vaporizer device, comprising:
at least one data processor; and
at least one memory storing instructions which, when executed by the at least one data processor, cause operations comprising:
determining that a total amount of energy consumed is less than a target maximum energy, wherein the vaporizer device comprises a cartridge configured to contain a vaporizable material, wherein the total amount of energy consumed represents a percentage of the vaporizable material that is depleted;
obtaining a predetermined dose indicative of a preset amount of aerosol to generate for a single use of the vaporizer device wherein the predetermined dose is indicative of the preset amount of aerosol associated with the cartridge and accessible to the at least one data processor, wherein the predetermined dose is defined by a preset amount of energy to be applied to generate the preset amount of aerosol;
applying, to a heating element in the cartridge, the preset amount of energy defining the predetermined dose to generate the preset amount of aerosol, wherein the preset amount of energy defining the predetermined dose is applied in response to the total amount of energy consumed being less than the target maximum energy;
determining, based on determining that the total amount of energy consumed is less than the target maximum energy, whether a timeout period has elapsed following completion of the single use; and
applying, based on determining that the timeout period has elapsed, the preset amount of energy defining another predetermined dose to generate the preset amount of aerosol,
wherein the preset amount of aerosol is generated by heating the vaporizable material using the preset amount of energy defining the predetermined dose.

12. The vaporizer device of claim 11, wherein data indicative of the preset amount of aerosol is stored on a near-field communication tag contained on at least a portion of the cartridge, wherein the at least one data processor is configured to obtain data stored on the near-field communication tag.

13. The vaporizer device of claim 11, wherein one or more of a value of the total amount of energy consumed, a fixed dose cartridge identifier, a value of dose size, a value of the target maximum energy, a cartridge lock identifier, a number of doses consumed, a dose size setting, a target number of doses, a dose control setting, and a time and date stamp are associated with the cartridge and accessible to the at least one data processor.

14. The vaporizer device of claim 13, wherein the application of the preset amount of energy is based on one or more of the fixed dose cartridge identifier, the cartridge lock identifier, and the dose control setting.

15. The vaporizer device of claim 13, wherein the instructions, when executed, cause operations further comprising:
modifying, following the application of the preset amount of energy, one or more of the value of the total amount of energy consumed, the number of doses consumed, and the time and date stamp.

16. The vaporizer device of claim 13, wherein the instructions, when executed, cause operations further comprising:
determining, based on the value of the total amount of energy consumed and the value of the target maximum energy, a number of doses remaining in the cartridge.

17. The vaporizer device of claim 16, wherein the instructions, when executed, cause operations further comprising:
modifying, in response to a determination of no doses remaining in the cartridge, the cartridge lock identifier.

18. The vaporizer device of claim 13, wherein the instructions, when executed, cause operations further comprising:
providing, to a user device in communication with the at least one data processor for display on the user device, one or more of data indicative of the preset amount of aerosol, the value of the total amount of energy consumed, the fixed dose cartridge identifier, the value of dose size, the value of the target maximum energy, the cartridge lock identifier, the number of doses consumed, the dose size setting, the target number of doses, the dose control setting, and the time and date stamp.

19. The vaporizer device of claim 11, wherein the preset amount of aerosol is one or more of a preconfigured amount and adjustable by a user through an application executed on a user device in communication with the at least one data processor.

20. A non-transitory computer readable medium storing instructions, which when executed by at least one data processor, result in operations comprising:
determining, by a controller of a vaporizer device, that a total amount of energy consumed is less than a target maximum energy, wherein the vaporizer device comprises a cartridge configured to contain a vaporizable material, wherein the total amount of energy consumed represents a percentage of the vaporizable material that is depleted;
obtaining, by the controller of the vaporizer device, a predetermined dose indicative of a preset amount of aerosol to generate for a single use of the vaporizer device, wherein the predetermined dose is indicative of the preset amount of aerosol associated with the cartridge and accessible to the controller, wherein the predetermined dose is defined by a preset amount of energy to be applied to generate the preset amount of aerosol;
applying, by the controller and to a heating element in the cartridge, the preset amount of energy defining the predetermined dose to generate the preset amount of aerosol, wherein the preset amount of energy defining the predetermined dose is applied in response to the total amount of energy consumed being less than the target maximum energy;
determining, based on determining that the total amount of energy consumed is less than the target maximum energy, whether a timeout period has elapsed following completion of the single use; and
applying, based on determining that the timeout period has elapsed, the preset amount of energy defining another predetermined dose to generate the preset amount of aerosol,
wherein the preset amount of aerosol is generated by heating the vaporizable material using the preset amount of energy defining the predetermined dose.

* * * * *